US010835512B2

(12) United States Patent
Soni et al.

(10) Patent No.: US 10,835,512 B2
(45) Date of Patent: *Nov. 17, 2020

(54) METHODS OF TREATING RESPIRATORY SYNCYTIAL VIRUS INFECTIONS

(71) Applicant: Respivant Sciences GmbH, Basel (CH)

(72) Inventors: Pravin Soni, Sunnyvale, CA (US); William Gerhart, Del Mar, CA (US); Manfred Keller, Munich (DE); Ahmet Tutuncu, Del Mar, CA (US)

(73) Assignee: Respivant Sciences GmbH, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/507,889

(22) Filed: Jul. 10, 2019

(65) Prior Publication Data

US 2019/0328700 A1 Oct. 31, 2019

Related U.S. Application Data

(63) Continuation of application No. 15/232,747, filed on Aug. 9, 2016, now abandoned, which is a continuation of application No. PCT/US2015/015033, filed on Feb. 9, 2015.

(60) Provisional application No. 62/105,453, filed on Jan. 20, 2015, provisional application No. 61/978,711, filed on Apr. 11, 2014, provisional application No. 61/971,709, filed on Mar. 28, 2014, provisional application No. 61/937,928, filed on Feb. 10, 2014.

(51) Int. Cl.
*A61K 31/352* (2006.01)
*A61K 9/00* (2006.01)
*A61K 9/12* (2006.01)
*A61K 47/02* (2006.01)
*A61K 9/08* (2006.01)

(52) U.S. Cl.
CPC .......... *A61K 31/352* (2013.01); *A61K 9/0073* (2013.01); *A61K 9/0075* (2013.01); *A61K 9/0078* (2013.01); *A61K 9/08* (2013.01); *A61K 9/12* (2013.01); *A61K 47/02* (2013.01)

(58) Field of Classification Search
None
See application file for complete search history.

(56) References Cited

U.S. PATENT DOCUMENTS

| | | |
|---|---|---|
| 3,419,578 A | 12/1968 | Fitzmaurice |
| 3,598,122 A | 8/1971 | Zaffaroni |
| 3,598,123 A | 8/1971 | Zaffaroni |
| 3,683,320 A | 8/1972 | Woods |
| 3,686,320 A | 8/1972 | Fitzmaurice |
| 3,686,412 A | 8/1972 | Fitzmaurice |
| 3,710,795 A | 1/1973 | Higuchi |
| 3,720,690 A | 3/1973 | King |
| 3,731,683 A | 5/1973 | Zaffaroni |
| 3,742,951 A | 7/1973 | Zaffaroni |
| 3,777,033 A | 12/1973 | Fitzmaurice |
| 3,790,580 A | 2/1974 | Johnson |
| 3,814,097 A | 6/1974 | Ganderton |
| 3,921,636 A | 11/1975 | Zaffaroni |
| 3,972,995 A | 8/1976 | Tsuk |
| 3,993,072 A | 11/1976 | Zaffaroni |
| 3,993,073 A | 11/1976 | Zaffaroni |
| 3,996,934 A | 12/1976 | Zaffaroni |
| 4,031,894 A | 6/1977 | Urquhart |
| 4,060,084 A | 11/1977 | Chandrasekaran |
| 4,067,992 A | 1/1978 | Kingsley |
| 4,069,307 A | 1/1978 | Higuchi |
| 4,077,407 A | 3/1978 | Theeuwes |
| 4,151,273 A | 4/1979 | Chiou |
| 4,152,448 A | 5/1979 | Wardell |
| 4,189,571 A | 2/1980 | Bodor |
| 4,201,211 A | 5/1980 | Chandrasekaran |
| 4,229,447 A | 10/1980 | Porter |
| 4,230,105 A | 10/1980 | Harwood |
| 4,268,519 A | 5/1981 | Turner |
| 4,292,299 A | 9/1981 | Suzuki |
| 4,292,303 A | 9/1981 | Keith |
| 4,343,789 A | 8/1982 | Kawata |
| 4,362,742 A | 12/1982 | Sullivan |
| 4,476,116 A | 10/1984 | Anik |
| 4,496,086 A | 1/1985 | Duchadeau |
| 4,596,795 A | 6/1986 | Pitha |
| 4,634,699 A | 1/1987 | McDermed |
| 4,683,135 A | 7/1987 | Pecht |
| 4,755,386 A | 7/1988 | Hsiao |
| 4,804,678 A | 2/1989 | Augstein et al. |
| 4,847,286 A | 7/1989 | Tamaki |
| 4,871,865 A | 10/1989 | Lever |
| 4,923,892 A | 5/1990 | Lever |

(Continued)

FOREIGN PATENT DOCUMENTS

| | | |
|---|---|---|
| AU | 2012238334 | 11/2012 |
| AU | 2013200711 | 2/2013 |

(Continued)

OTHER PUBLICATIONS

"View of NCT024 78957 on Feb. 26, 2016." NCT02478957 on Feb. 26, 2016: ClinicalTrials.Gov Archive, Accessed Jan. 30, 2018 (4 pages). clinicaltrials.gov/archive/NCT024 78957/2016 02 26.
"View of NCT024 78957 on Sep. 28, 2016." NCT02478957 on Sep. 28, 2016: ClinicalTrials.Gov Archive, Accessed Jan. 30, 2018 (4 pages). clinicaltrials.gov/archive/NCT024 78957/2016 09 28.
"View of NCT02412020 on Apr. 7, 2015." NCT02412020 on Apr. 7, 2015: Clinica/Trials.Gov Archive, Accessed Jan. 30, 2018 (4 pages). clinicaltrials.gov/archive/NCT02412020/2015 04 07.

(Continued)

*Primary Examiner* — Jennifer A Berrios
(74) *Attorney, Agent, or Firm* — Fish & Richardson P.C.

(57) ABSTRACT

Compositions and methods for the treatment of respiratory syncytial virus infections are provided.

21 Claims, No Drawings

(56) References Cited

U.S. PATENT DOCUMENTS

| | | |
|---|---|---|
| 4,996,296 A | 2/1991 | Pecht |
| 5,049,389 A | 9/1991 | Radhakrishnan |
| 5,116,817 A | 5/1992 | Anik |
| 5,280,784 A | 1/1994 | Koehler |
| 5,281,420 A | 1/1994 | Kelm |
| 5,309,900 A | 5/1994 | Knoch |
| 5,312,046 A | 5/1994 | Knoch |
| 5,336,168 A | 8/1994 | Sibalis |
| 5,340,591 A | 8/1994 | Nakano |
| 5,456,923 A | 10/1995 | Nakamichi |
| 5,458,136 A | 10/1995 | Jaser |
| 5,461,695 A | 10/1995 | Knoch |
| 5,475,023 A | 12/1995 | Baskeyfield |
| 5,485,827 A | 1/1996 | Zapol et al. |
| 5,508,451 A | 4/1996 | Bhattacharya |
| 5,549,102 A | 8/1996 | Lintl |
| 5,552,436 A | 9/1996 | Clemente |
| 5,567,720 A | 10/1996 | Averback |
| 5,576,346 A | 11/1996 | Clemente |
| 5,618,842 A | 4/1997 | Della |
| 5,665,378 A | 9/1997 | Davis |
| 5,700,485 A | 12/1997 | Berde |
| 5,723,269 A | 3/1998 | Akagi |
| 5,739,136 A | 4/1998 | Ellinwood |
| 5,740,966 A | 4/1998 | Blaha-Schnabel |
| 5,753,208 A | 5/1998 | Nagy |
| 5,837,280 A | 11/1998 | Kenealy |
| 5,869,090 A | 2/1999 | Rosenbaum |
| 5,952,353 A | 9/1999 | Janicki et al. |
| 5,957,389 A | 9/1999 | Wunderlich |
| 6,000,394 A | 12/1999 | Blaha-Schnabel |
| 6,004,949 A | 12/1999 | Shima |
| 6,083,518 A | 7/2000 | Lindahl |
| 6,085,741 A | 7/2000 | Becker |
| 6,123,924 A | 9/2000 | Mistry et al. |
| 6,138,973 A | 10/2000 | Shepherd |
| 6,176,237 B1 | 1/2001 | Wunderlich |
| 6,207,684 B1 | 3/2001 | Aberg |
| 6,225,327 B1 | 5/2001 | Miller |
| 6,323,219 B1 | 11/2001 | Costanzo |
| 6,365,180 B1 | 4/2002 | Meyer |
| 6,391,452 B1 | 5/2002 | Antonsen |
| 6,433,040 B1 | 8/2002 | Dellamary et al. |
| 6,475,467 B1 | 11/2002 | Keller et al. |
| 6,482,390 B1 | 11/2002 | Hiscocks et al. |
| 6,503,481 B1 | 1/2003 | Thurston et al. |
| 6,513,519 B2 | 2/2003 | Gallem |
| 6,513,727 B1 | 2/2003 | Jaser |
| 6,585,958 B1 | 7/2003 | Keller et al. |
| 6,596,261 B1 | 7/2003 | Adjel et al. |
| 6,596,284 B1 | 7/2003 | Fleming et al. |
| 6,660,715 B2 | 12/2003 | Klibanov |
| 6,923,983 B2 | 8/2005 | Morgan |
| 6,929,801 B2 | 8/2005 | Klose |
| 6,946,144 B1 | 9/2005 | Jordan |
| 7,060,827 B2 | 6/2006 | Singh |
| 7,074,388 B2 | 7/2006 | Adjei et al. |
| 7,109,246 B1 | 9/2006 | Hawtin |
| 7,247,711 B2 | 7/2007 | Benson et al. |
| 7,250,165 B2 | 7/2007 | Heavener et al. |
| 7,258,872 B1 | 8/2007 | Wigmore |
| 7,345,037 B2 | 3/2008 | Garvey et al. |
| 7,427,471 B2 | 9/2008 | Scallon et al. |
| 7,481,995 B2 | 1/2009 | Dickinson et al. |
| 7,550,133 B2 | 6/2009 | Hale et al. |
| 7,566,743 B2 | 7/2009 | Glazman |
| 7,582,297 B2 | 9/2009 | Reed |
| 7,687,054 B2 | 3/2010 | Stefely et al. |
| 7,727,558 B2 | 6/2010 | Milstein et al. |
| 7,744,910 B2 | 6/2010 | Gschneidner et al. |
| 7,758,886 B2 | 7/2010 | Jauering et al. |
| 7,807,200 B2 | 10/2010 | Lipp et al. |
| 7,867,508 B1 | 1/2011 | Smith |
| 7,897,776 B2 | 3/2011 | Weingarten et al. |
| 7,955,597 B2 | 6/2011 | Giles-Komar et al. |
| 8,006,698 B2 | 8/2011 | Boehm |
| 8,088,935 B2 | 1/2012 | Pearson |
| 8,252,807 B2 | 8/2012 | Logsdon |
| 8,257,744 B2 | 9/2012 | Lopez-Belmonte Encina et al. |
| 8,258,268 B2 | 9/2012 | Wu et al. |
| 8,263,645 B2 | 9/2012 | Keller |
| 8,361,509 B2 | 1/2013 | Lopez-Belmonte Encina et al. |
| 8,383,778 B2 | 2/2013 | Hsieh et al. |
| 8,398,966 B2 | 3/2013 | Wu et al. |
| 8,410,309 B2 | 4/2013 | Leone-Bay et al. |
| 8,430,097 B2 | 4/2013 | Jinks et al. |
| 8,445,437 B2 | 5/2013 | Shi |
| 8,454,938 B2 | 6/2013 | Green et al. |
| 8,461,125 B2 | 6/2013 | Grunstein |
| 8,470,805 B2 | 6/2013 | Chen |
| 8,481,081 B2 | 7/2013 | Babcock et al. |
| 8,513,300 B2 | 8/2013 | Abbas |
| 8,578,933 B2 | 11/2013 | Remmeigas et al. |
| 8,586,044 B2 | 11/2013 | Thumbikat |
| 8,586,714 B2 | 11/2013 | Ghayur et al. |
| 8,617,517 B2 | 12/2013 | Elmaleh |
| 8,624,002 B2 | 1/2014 | Gu et al. |
| 8,716,450 B2 | 5/2014 | Ghayur et al. |
| 8,722,855 B2 | 5/2014 | Ghayur et al. |
| 8,785,383 B2 | 7/2014 | Shi |
| 8,808,786 B2 | 8/2014 | Jinks et al. |
| 8,822,645 B2 | 9/2014 | Ghayur et al. |
| 8,853,365 B2 | 10/2014 | Wu et al. |
| 9,011,941 B2 | 4/2015 | Jones et al. |
| 9,029,508 B2 | 5/2015 | Ghayur et al. |
| 9,035,027 B2 | 5/2015 | Ghayur et al. |
| 9,035,085 B2 | 5/2015 | Rath et al. |
| 9,046,513 B2 | 6/2015 | Ghayur et al. |
| 9,095,621 B2 | 8/2015 | Riggs-Sauthier et al. |
| 9,109,026 B2 | 8/2015 | Ghayur et al. |
| 9,181,577 B2 | 11/2015 | Thumbikat |
| 9,198,859 B2 | 12/2015 | Keller |
| 9,226,983 B2 | 1/2016 | Benatuil et al. |
| 9,265,749 B2 | 2/2016 | Gerhart et al. |
| 9,284,279 B2 | 3/2016 | Ford et al. |
| 9,321,836 B2 | 4/2016 | Heavener et al. |
| 9,333,174 B2 | 5/2016 | Batycky et al. |
| 9,353,181 B2 | 5/2016 | Benson et al. |
| 9,439,862 B2 | 9/2016 | Weers et al. |
| 9,447,184 B2 | 9/2016 | Wu et al. |
| 9,492,408 B2 | 11/2016 | Leikauf |
| 9,574,004 B2 | 2/2017 | Ardeleanu et al. |
| 9,592,220 B2 | 3/2017 | Gonda |
| 9,592,293 B2 | 3/2017 | Wu |
| 9,663,587 B2 | 5/2017 | Hsieh et al. |
| 9,670,276 B2 | 6/2017 | Lacy et al. |
| 9,707,206 B2 | 7/2017 | Gerhart et al. |
| 9,744,314 B2 | 8/2017 | Keller et al. |
| 9,755,314 B2 | 8/2017 | Keller et al. |
| 9,855,276 B2 | 1/2018 | Elmaleh |
| 1,039,107 A1 | 8/2019 | Gerhart et al. |
| 1,039,867 A1 | 9/2019 | Gerhart et al. |
| 2002/0009491 A1 | 1/2002 | Rothbard |
| 2004/0013734 A1 | 1/2004 | Babcock |
| 2004/0120956 A1 | 6/2004 | Song et al. |
| 2004/0204399 A1 | 10/2004 | Osbakken et al. |
| 2005/0008638 A1 | 1/2005 | Lu et al. |
| 2005/0033029 A1 | 2/2005 | Lu et al. |
| 2005/0038243 A1 | 2/2005 | Singh et al. |
| 2005/0113317 A1 | 5/2005 | Robinson et al. |
| 2005/0129695 A1 | 6/2005 | Mercken et al. |
| 2005/0191246 A1 | 9/2005 | Bechtold-Peters et al. |
| 2005/0209141 A1 | 9/2005 | Silver |
| 2005/0232923 A1 | 10/2005 | Yan et al. |
| 2005/0244339 A1 | 11/2005 | Jauernig |
| 2005/0266005 A1 | 12/2005 | Heavner et al. |
| 2006/0002995 A1 | 1/2006 | Harwigsson |
| 2006/0069124 A1 | 3/2006 | Rao et al. |
| 2006/0078558 A1 | 4/2006 | Whitsett |
| 2006/0246075 A1 | 11/2006 | Mercken et al. |
| 2007/0036860 A1 | 2/2007 | Wigmore |
| 2007/0086981 A1 | 4/2007 | Meijer |
| 2007/0193577 A1 | 8/2007 | Keller |
| 2007/0219223 A1 | 9/2007 | Wilson et al. |

(56) References Cited

U.S. PATENT DOCUMENTS

| | | |
|---|---|---|
| 2008/0032918 A1 | 2/2008 | Silver |
| 2008/0078382 A1 | 4/2008 | LeMahieu et al. |
| 2008/0194676 A1 | 8/2008 | Abbas |
| 2008/0214491 A1 | 9/2008 | Logsdon |
| 2008/0227704 A1 | 9/2008 | Kamens |
| 2009/0025713 A1 | 1/2009 | Keller et al. |
| 2009/0081274 A1 | 3/2009 | Silver |
| 2009/0239916 A1 | 9/2009 | Tanaka |
| 2009/0318545 A1 | 12/2009 | Silver |
| 2010/0028351 A1 | 2/2010 | Mercken et al. |
| 2010/0074901 A1 | 3/2010 | Mercken et al. |
| 2010/0087455 A1 | 4/2010 | Gant |
| 2010/0143268 A1 | 6/2010 | Kellaway et al. |
| 2010/0150898 A1 | 6/2010 | Boucher, Jr. |
| 2010/0196286 A1 | 8/2010 | Armer |
| 2010/0233079 A1 | 9/2010 | Jakob et al. |
| 2010/0260668 A1 | 10/2010 | Ghayur et al. |
| 2010/0316576 A1 | 12/2010 | Keller et al. |
| 2011/0044980 A1 | 2/2011 | Ghayur et al. |
| 2011/0112183 A1 | 5/2011 | Riggs-Sauthier |
| 2011/0195924 A1 | 8/2011 | Logsdon |
| 2011/0223216 A1 | 9/2011 | Da Rocha et al. |
| 2011/0250130 A1 | 10/2011 | Benatuil et al. |
| 2012/0076859 A1 | 3/2012 | Hofmann |
| 2012/0118991 A1 | 5/2012 | Keller |
| 2012/0132204 A1 | 5/2012 | Lucking et al. |
| 2012/0201746 A1 | 8/2012 | Liu et al. |
| 2012/0258108 A1 | 10/2012 | Ghayur et al. |
| 2012/0275996 A1 | 11/2012 | Hsieh |
| 2013/0017247 A1 | 1/2013 | Harish et al. |
| 2013/0171059 A1 | 7/2013 | Ghayur et al. |
| 2013/0253475 A1 | 9/2013 | Wang |
| 2014/0007867 A1 | 1/2014 | Bruin et al. |
| 2014/0014094 A1 | 1/2014 | Warner et al. |
| 2014/0065219 A1 | 3/2014 | Bosch et al. |
| 2014/0083422 A1 | 3/2014 | Arvidsson et al. |
| 2014/0109900 A1 | 4/2014 | Jinks |
| 2014/0140927 A1 | 5/2014 | Elmaleh |
| 2014/0242174 A1 | 8/2014 | Walker |
| 2014/0271457 A1 | 9/2014 | Ghayur et al. |
| 2015/0018396 A1 | 1/2015 | Lee et al. |
| 2015/0038530 A1 | 2/2015 | Abraham et al. |
| 2015/0040901 A1 | 2/2015 | Parkes |
| 2015/0057299 A1 | 2/2015 | Ford et al. |
| 2015/0072961 A1 | 3/2015 | Yu et al. |
| 2015/0107589 A1 | 4/2015 | Longest et al. |
| 2015/0224077 A1 | 8/2015 | Gerhart et al. |
| 2015/0224078 A1 | 8/2015 | Gerhart et al. |
| 2015/0273119 A1 | 10/2015 | Heo et al. |
| 2015/0290135 A1 | 10/2015 | Chamarthy et al. |
| 2015/0297557 A1 | 10/2015 | Gerhart et al. |
| 2015/0306107 A1 | 10/2015 | Chen |
| 2015/0320747 A9 | 11/2015 | Schmittmann |
| 2015/0337315 A1 | 11/2015 | Grunstein |
| 2016/0106704 A1 | 4/2016 | Elmaleh et al. |
| 2016/0106802 A1 | 4/2016 | Paterson |
| 2016/0263257 A1 | 9/2016 | Elmaleh et al. |
| 2016/0280791 A1 | 9/2016 | Ghayur et al. |
| 2016/0310681 A1 | 10/2016 | Finke et al. |
| 2016/0319026 A1 | 11/2016 | Ghayur et al. |
| 2016/0346245 A1 | 12/2016 | Gerhart et al. |
| 2016/0346246 A1* | 12/2016 | Gerhart .................. A61K 9/12 |
| 2016/0347844 A1 | 12/2016 | Dekruyff et al. |
| 2016/0367519 A1 | 12/2016 | Gerhart et al. |
| 2016/0367520 A1 | 12/2016 | Gerhart et al. |
| 2016/0375135 A1 | 12/2016 | Gschneidner et al. |
| 2017/0107574 A1 | 4/2017 | Ziesche |
| 2017/0196904 A1 | 7/2017 | Gotz et al. |
| 2017/0218091 A1 | 8/2017 | Ambrosi |
| 2017/0235918 A1 | 8/2017 | Hagen et al. |
| 2017/0273941 A1 | 9/2017 | Gerhart et al. |
| 2017/0275397 A1 | 9/2017 | Park et al. |
| 2017/0335393 A1 | 11/2017 | Ziesche |
| 2017/0349947 A1 | 12/2017 | Ziesche |
| 2019/0307721 A1 | 10/2019 | Soni |
| 2019/0328700 A1 | 10/2019 | Soni |
| 2019/0388385 A1 | 12/2019 | Soni |
| 2019/0388386 A1 | 12/2019 | Gerhart et al. |

FOREIGN PATENT DOCUMENTS

| | | |
|---|---|---|
| AU | 2015200579 | 2/2015 |
| AU | 2016222339 | 3/2016 |
| EP | 0163683 | 12/1985 |
| EP | 0183457 | 6/1986 |
| EP | 0413583 | 5/1990 |
| EP | 0304802 | 3/1993 |
| EP | 0587264 | 10/1994 |
| EP | 1128826 | 1/2004 |
| EP | 1754492 | 2/2007 |
| EP | 2364696 | 9/2011 |
| EP | 2391618 A2 | 12/2011 |
| EP | 1858485 | 9/2013 |
| EP | 2248517 B1 | 3/2014 |
| EP | 1874270 | 8/2015 |
| EP | 2533777 | 7/2016 |
| EP | 3104853 | 10/2019 |
| GB | 2145107 | 3/1985 |
| JP | S61143318 | 7/1986 |
| JP | H06072869 | 3/1994 |
| JP | 2012-526084 | 10/2012 |
| WO | WO8502541 | 6/1985 |
| WO | WO9505816 | 3/1995 |
| WO | WO-9631204 | 10/1996 |
| WO | WO9831346 | 7/1998 |
| WO | WO9916421 | 4/1999 |
| WO | WO-0027392 A1 | 5/2000 |
| WO | WO-0042993 A2 | 7/2000 |
| WO | WO0113892 | 3/2001 |
| WO | WO0212502 | 2/2002 |
| WO | WO-03045331 A2 | 6/2003 |
| WO | WO2004039826 | 5/2004 |
| WO | WO2005028511 | 3/2005 |
| WO | WO-2005063732 | 7/2005 |
| WO | WO2005077189 | 8/2005 |
| WO | WO-2005115468 | 12/2005 |
| WO | WO2006105538 | 10/2006 |
| WO | WO2007103970 | 9/2007 |
| WO | WO2008116165 | 9/2008 |
| WO | WO-2009045291 | 4/2009 |
| WO | WO2009052125 | 4/2009 |
| WO | WO-2009131695 | 10/2009 |
| WO | WO-2010042504 | 4/2010 |
| WO | WO-2010088455 | 8/2010 |
| WO | WO-2010128111 | 11/2010 |
| WO | WO-2012031445 | 3/2012 |
| WO | WO2012061374 | 5/2012 |
| WO | WO-201406631 | 5/2014 |
| WO | WO2014115098 | 7/2014 |
| WO | WO2015079198 | 6/2015 |
| WO | WO-2015120389 | 8/2015 |
| WO | WO2015120392 | 8/2015 |
| WO | WO2015161510 | 10/2015 |
| WO | WO2015185195 | 12/2015 |
| WO | WO2015185653 | 12/2015 |
| WO | WO2015185658 | 12/2015 |
| WO | WO2016004389 | 1/2016 |
| WO | WO2016011254 | 1/2016 |
| WO | WO2016064908 | 4/2016 |
| WO | WO2017011729 | 1/2017 |
| WO | WO2017027387 | 2/2017 |
| WO | WO2017027402 | 2/2017 |
| WO | WO2017048860 | 3/2017 |
| WO | WO2018044942 | 3/2018 |

OTHER PUBLICATIONS

"View of NCT02412020 on Apr. 8, 2015." NCT02412020 on Apr. 8, 2015: ClinicalTrials.Gov Archive, Accessed Jan. 30, 2018 (4 pages). clinicaltrials.gov/archive/NCT02412020/2015 04 08.

"View of NCT02412020 on Sep. 25, 2015." NCT02412020 on Sep. 25, 2016: ClinicalTrials.Gov Archive, Accessed Jan. 30, 2018 (4 pages). clinicaltrials.gov/archive/NCT02412020/2015 09 25.

(56) References Cited

OTHER PUBLICATIONS

"View of NCT02412020 on Feb. 19, 2016." NCT02412020 on Feb. 19, 2016: ClinicalTrials.Gov Archive, Accessed Jan. 30, 2018 (4 pages). clinicaltrials.oov/archive/NCT02412020/2016 02 19.
"View of NCT02478957 on Jun. 22, 2015." NCT02478957 on Jun. 22, 2015: ClinicalTrials.Gov Archive, Accessed Jan. 30, 2018 (4 pages). clinicaltrials.gov/archive/NCT024 78957/2015 06 22.
"View of NCT02478957 on Sep. 25, 2015." NCT02478957 on Sep. 25, 2015: ClinicalTrials.Gov Archive, Accessed Jan. 30, 2018 (4 pages). clinicaltrials.gov/archive/NCT024 78957/2015 09 25.
"View of NCT02696499 on Mar. 1, 2016." NCT02696499 on Mar. 1, 2016: ClinicalTrials.Gov Archive, Accessed Jan. 30, 2018 (4 pages). clinicaltrials.gov/archive/NCT02696499/2016 03 01.
"View of NCT02696499 on May 3, 2016." NCT02696499 on May 3, 2016: Clinica/Tria/s.Gov Archive, Accessed Jan. 30, 2018 (4 pages). clinicaltrials.oov/archive/NCT02696499/2016 05 03.
"View of NCT02696499 on Apr. 5, 2017." NCT02696499 on Apr. 5, 2017: ClinicalTrials.Gov Archive, Accessed Jan. 30, 2018 (4 pages). clinicaltrials.gov/archive/NCT02696499/2017 04 05.
Advisory Action for U.S. Appl. No. 14/617,221, dated Aug. 19, 2016.
Afrin, B. Lawrence, "Presentation, Diagnosis, and Management of Mast Cell Activation Syndrome," Mast Cells (2013) Chapter 6 (6 pages).
Allistone et al., The effect of intravenous sodium cromoglycate on the bronchoconstriction induced by sulphur dioxide inhalation in man. Clinical Science, 68:227-232 (1985).
Allowed Claims and Notice of Allowance of U.S. Appl. No. 15/117,711, dated Feb. 13, 2018. (11 pages).
Anderson, et al., "Sodium Cromoglycate Alone and in Combination with Montelukast on the Airway Response to Mannitol in Asthmatic Subjects," J Asthma, 47:429-433 (2010).
Ariyanayagam et al., Topical sodium cromoglycate in the management of atopic eczema-a controlled trial. British Journal of Dermatology, 112:343-348 (1985).
Ashton et al., The absorption, metabolism and excretion of disodium cromoglycate in nine animal studies. Toxicology and Applied Pharmacology, 26:319-328 (1973).
Asmus et al., "Pulmonary function response to EDTA, and additive nebulized bronchodilators," J. Allergy Clin Immunology, 107(1):68-71 (2001).
Aswania et al., Relative bioavailability of sodium cromoglycate to the lung following inhalation, using urinary excretion. British Journal of Clinical Pharmacology, 47:613-618 (1999).
Aswania et al.,"Relative lung and bioavailability of generic sodium cromoglycate inhalers used without a spacer device," Pulmonary Pharmacology & Therapeutics, 14:129-133 (2001).
Auty et al., Respiratory tract deposition of sodium cromoglycate is highly dependent upon technique of inhalation using the spin haler. British Journal Dis. Chest, 81 :371-380 (1987).
Balzar, et al., "Mast Cell Phenotype, Location, and Activation in Severe Asthma Data from the Severe Asthma Research Program," Am J Repir Crit Care Med. 183:299-309, 2010.
Balzar, et al., "Relationships of Small Airway Chymase-Positive Mast Cells and Lung Function in Severe Asthma," Am J Respir Crit Care Med, 171 :431-439, (2005).
Barnes, P.J., "New concepts in the pathogenesis of bronchial hyperresponsiveness and asthma," J Allergy Clin Immunol., 83:1013-1026, (1989).
Behr, et al., "Lung Depostition of a Liposomal Cyclosporine a Inhalation Solution in Patients after Lung Transplantation," J Med Pulm Drug Delive., 22(2):121-129, (2009).
Benson, et al., "Uptake of disodium cromoglycate in obstructive airways disease," Clinical Allergy, 3:389-394, (1973).
Bizzintino, et al., "Association between human rhinovirus C and severity of acute asthma in children," Eur RepirJ., 37:1037-1042, (2011).
Bourdin, et al., "Upper airway 1 :Allergic rhinitis and asthma : united disease through epithelial cells," Thorax, 64:999-1004, (2009).

Brannan, et al., "Inhibition of mast cell PGD2 release protects against mannitol-induced airway narrowino," Eur RespirJ., 27:944-950, (2006).
Burgel, et al., "Update on the roles of distal airways in asthma," Eur Repir Rev., 18:80-95, (2009).
Chen, Chronic cough. Medscape Reference. Drugs, Diseases & Procedures. 5 pages, Updated May 13, 2014.
Cho, A., Recent Advances in Oral Prod rug Discovery. Annual Reports in Medicinal Chemistry, vol. 41, 395-407, (2006).
Cieslewicz, et al., "The late, but not early, asthmatic response is dependent on IL-5 and correlates with eosinophil infiltration," J. Clin Inv., 104(3):301-308, (1999).
Clinicaltrialsregister.eu. "Randomized, Double-blind, Placebo-controlled, Crossover Design, Efficacy and Safety Study with PA101 in Patients with Indolent Systemic Mastocytosis," Clinical Trials Register. Dec. 11, 2014. Accessed Jan. 30, 2018 (6 pages). [online] Available at: https://www.clinicaltrialsregister.eu/ctr-search/trial/2014-004113-85/DE.
Clinicaltrialsregister.eu. "Randomized, Double-blind, Placebo-controlled, Crossover Design, Efficacy and Safety Study with PA101 in Patients with Indolent Systemic Mastocytosis," Clinical Trials Register. Dec. 22, 2014. Accessed Jan. 30, 2018 (4 pages). [online] Available at: https://www.clinicaltrialsreaister.eu/ctr-search/trial/2014-004113-85/ES.
Clinicaltrialsregister.eu. "Randomized, Double-blind, Placebo-controlled, Crossover Design, Efficacy and Safety Study with PA101 in Patients with Indolent Systemic Mastocytosis," Clinical Trials Register. Dec. 4, 2014. Accessed Jan. 30, 2018 (5 pages). [online] Available at: https://www.clinicaltrialsregister.eu/ctr-search/trial/2014-004113-85/NL.
Clinicaltrialsregister.eu. "Treatment of Chronic Cough with PA 101," Clinical Trials Register. Dec. 11, 2014. Accessed Jan. 30, 2018 (6 pages). [online] Available at: https://www.clinicaltrialsregister.eu/ctr-search/trial/2014-004025-40/NL.
Clinicaltrialsregister.eu. "Treatment of Chronic Cough with PA 101," Clinical Trials Register. Jan. 6, 2015. Accessed Jan. 30, 2018 (6 pages). [online] Available at: https://www.clinicaltrialsreqister.eu/ctr-search/trial/2014-004025-40/GB.
Clinicaltrialsregister.eu. "Treatment of Uremic Pruritus with Inhaled PA 101 B in Patients with End-Stage Renal Disease Requiring Hemodialysis," Clinical Trials Register. Jan. 13, 2016. Accessed Jan. 30, 2018 (6 pages). [online] Available at: https://www.clinicaltrialsregister.eu/ctr-search/trial/2015-004 794-33/PL.
Coates, et al., "Rapid Pulmonary Delivery of Inhaled Tobramycin for Pseudomonas Infection in Cystic Fibrosis: A Pilot Project," Pediatr Pulmonol., 43:753-759, (2008).
Cox, et al., "Solid-State Chemistry of Cromolyn Sodium (Disodium Cromoglycate)," J Pharm Sci., 60:1458-1465, (1971).
Curry, et al., "Disposition of Disodium Cromoglycate Administered in Three Particle Sizes," British Journal of Clinical Pharmacology, 2:267-270, (1975).
Deliargyris, Efthymios N., et al., "Mast cell tryptase: a new biomarker in patients with stable coronary artery disease." Atherosclerosis 178.2 (2005): 381-386.
Diaz, et al., "Bronchoalevolar lavage in asthma. The effect of disodium cromoglycate (cromolyn) on leukocyte counts, immuno-globulins, and complement," J Allergy Clin Immunol., 74:41-48, (1984).
Dixon et al., The Action of sodium cromoglycate on "C" fibre endings in the dog lung. Br. J. Pharm., 70:11-13 (1980).
Doenicke, A., et al., "Osmolalities of propylene Glycol-Contaning Drug Formulations for Parenteral Use. Should Propylene Glycol be used as a Solvent?" Anesth. Analg., 75:431 (5), (1992).
Edwards et al., Oral and inhaled sodium cromoglycate in the management of systemic mastocytosis: a case report. Journal of Medical Case Reports, 4:193-198 (2010).
Edwards, A.M., et al., "Oral and inhaled sodium cromoglycate in the management of systemic mastocvtosis: a case report," Journal of Medical Case Reports, 4:193-198, (2010).
Edwards, et al., "Inhaled sodium cromoglycate in children with asthma," Thorax 57:282, (2002).
Edwards, et al.,"Sodium cromoglycate in childhood asthma," Thorax, 56:331-332, (2001).

(56) References Cited

OTHER PUBLICATIONS

Eggleston, P.A., "Exercise-Induces Asthma," Clin Rev Allergy, 1:19-37, (1983).
Emisphere Technologies, Inc., The facts on . . . Oral Cromolyn Sodium. 2 pages (2006).
Estfan and LeGrand, Management of cough in advanced cancer. Journal of Supportive Oncology, 2(6):523-527 (2004).
FDA Guidance for Industry, "Bioavailability and Bioequivalence Studies for Nasal Aerosols and Nasal Sprays for Local Action," Biopharmaceutics, (2003) 37 Pgs.
Final Rejection for U.S. Appl. No. 14/617,221, dated Jun. 16, 2016.
Finlay, WH, and AR Martin, "Recent advances in predictive understanding respiratory tract deposition." Journal of Aerosol Medicine, 21:189-205 (2008).
Francis, Heather, and Cynthia J Meininger. "A review of mast cells and liver disease: What have we learned?." Digestive and Liver Disease 42.8 (2010): 529-536.
Fukasawa, et al., "The Effects of Disodium Cromoglycate on Enhanced Adherence of Haemophilus influenzae to A549 Cells Infected With Respiratory Syncytial Virus," Pediatric Research, (2009), 66(2):168-173.
Furukawa, et al., "A Double-Blind Study Comparing the Effectiveness of Cromolyn Sodium and Sustained-Release Theophylline in Childhood Asthma," Pediatrics, (1984), 74(4):453-459.
Furusho, et al., "The combination of nebulized sodium cromoglycate and salbutamol in the treatment of moderate-to-severe asthma in children," Pediatric Allergy Imminol., (2002), 13:209-216.
Hamid et al., "Inflammation of small airways in asthma," J Allergy Clin Immunol., (1997), 100:44-51.
Hammoudeh et al., "Diffuse Alveolar Haemorrhage with ANCA associated vasculitis-review of literature," British Journal of Medical Practitioners (BJMP), 2011, 4(1):a402, 5 pages.
Hargreaves and Benson, Inhaled sodium cromoglycate in angiotensin-converting enzyme inhibitor cough. Lancet, 345:13-16 (1995).
Hashimoto et al., "DSCG Reduces RSV-Induced Illness in RSV-Infected Mice," J Med Virol., (2009) 81 :354-361.
Hemmati A.A. et al., "The role of sodium cromolyn in treatment of paraquat-induced pulmonary fibrosis in rat", Pharmacolooical Research, (2002), 46(3):229-234.
Hidari et al., "In Vitro and in Vivo Inhibitory Effects of Disodium Cromoglycate on Influenza Virus Infection," Biol Pharm Bull., (2004), 27(6):825-830.
Hiller et al., "Physical Properties, Hygroscopicity and Estimated Pulmonary Retention of Various Therapeutic Aerosols," Chest, (1980), 77:318-321.
Horan, Richard F., et al., "Cromolyn sodium in the management of systemic mastocytosis." Journal of Allergy and Clinical Immunology 85.5 (1990): 852-855.
Hori et al., FDA approved asthma therapeutic agent impacts amyloid B in the brain in a transgenic model of Alzheimer's disease. The Journal of Biological Chemistry, Affinity Sites, • Published online on Dec. 2, 2014 as Manuscript M114.586602.
Hoshino et al., "A comparative study of the effects of ketotifen, disodium cromoglycate; and beclomethasone dipropionate on bronchial mucosa and asthma symptoms in patients with atopic asthma," Respir Med., (1998), 92:942-950.
Hoshino et al., "The effect of inhaled sodium cromoglycate on cellular infiltration into the bronchial mucosa and the expression of adhesion molecules in asthmatics," Eur Respir J., (1997), 10:858-865.
Intal FDA Label "Intal® Nebulizer Solution," Aventis Pharmaceuticals, Inc. (2003).
Intal Spincaps, Sodium Cromoglicate 20 mg capsules, Feb. 2007, 4 pages.
Ivax Pharmaceuticals, Crornolyn Sodium—Cromolyn sodium inhalation solution prescribing information, accessed at https://dailymed.nlm.nih.gov/dailymed/drugInfo.cfm?setid=8fe37a7a-edd6-4733-bb7e-e01c1906aeba May 2, 2016.
Iyer and Lim, Chronic Cough: An Update. Mayo Clinic Proceedings. 88(10):1115-1126 (2013).

Jones, et al., "Increased Alveolar Epithelial Permeability in Cigarette Smokers," The Lancet, 1980, 1:66-68.
Kano, et al., "Change in osmolarity of disodium cromoglycate solution and protection against exercise-induced bronchospasm in children with asthma," Eur RespirJ., (1996), 9:1891-1895.
Kato et al. Plasma Concentrations of Disodium Cromoglycate After Various Inhalation Methods in Healthy Subjects. British Journal of Clinical Pharmacology. 48(2) 154-157 (1999).
Keller et al., "Importance of the Inhaler System and Relative Humidity on the Fine Particle Dose (FPO) of Disodium Cromoglycate (DSCG)," RODD Europe, (2007), 307-310.
Keller et al., Did inappropriate delivery systems hamper therapeutic efficacy of Di-Sodium-Cromo-Glycate (DSCG)? Time for a Reappraisal. Poster Presentation. PARI Pharma: ISAM, P-089, 1 page (2011 ).
Keller et al., Have inadequate delivery systems hampered the clinical success of inhaled disodium cromoglycate? Time for reconsideration. Expert Opin. Drug Delivery, 8(1):1-17 (2011).
Keller, M. "Innovations and perspectives of metered dose inhalers in pulmonary drug delivery," IntJ Pharma., (1999), 186:81-90.
Kim et al., "Nasal and Sinus Inflammation in Chronic Obstructive Pulmonary Disease, COPD," Journal of Chronic Obstructive Pulmonary Disease, 2007, 4:163-166.
Kippelen et al., "Effect of Sodium Cromoglycate on Mast Cell Mediators during Hyperpnea in Athletes," Med Sci Sports Exerc., (2010) 1853-1860.
Kitabis Pak reference (www.rxlist.com/kitabis-pak-drug.htm, 2 pages, 2011.
Kohler et al., "Lung deposition after inhalation with various nebulisers in preterm infants," Arch Dis Child Fetal Neonatal., (2008), 93(4):F275-F279.
Kohler, et al., "Does Wearing a Noseclip during Inhalation Improve Lung Deposition?" J. Aerosol Med., (2004), 17(2):116-122.
Kohler, et al., "Lung Deposition in Cystic Fibrosis Patients Using an Ultrasonic or a Jet Nebulizer," JAMA, (2003), 16(1):37-46.
Korppi et al., "Disodium Cromoglycate in Asthma—Worth to Be Re-appraised," Allergol Int., (2008), 57:183.
Krawiec et al., "Inhaled Nonsteroidal Anti-inflammatory Medications in the Treatment of Asthma," Respir Care Clin N Am., (1999), 5(4):555-574 (Abstract Only).
Kupper T et al., "Cromoglycate, reproterol, or both-what's best for exercise-induced asthma", Sleep and Breathing; International Journal of the Science and Practice of Sleep Medicine, Springer, (2012)e-pub Dec. 2011, 16(4):1229-1235.
Larsson, et al., "Sodium cromoglycate attenuates pulmonary inflammation without influencing bronchial responsiveness in healthy subjects exposed to organic dust," Clin Exp Allergy, (2001), 31:1356-1368.
Latimer et al., Inhibition by sodium cromoglycate of bronchoconstriction stimulated by respiratory heat loss: comparison or pressurized aerosol and powder. Thorax, 39:277-281 (1984).
Laube et al., "The efficacy of slow versus faster inhalation of cromolyn sodium in protecting against allergen challenge in patients with asthma," J Allergy Clin Immunol., (1998), 101:475-483.
Lavinka and Dong, Molecular signaling and targets from itch: lessons for cough. Cough, 9:8, 13 pages (2013).
Leitch, A.G. et al., "Disodium cromoglycate relieves symptoms in symptomatic young smokers. A double blind placebo controlled trial", Allergy, (1984), 39(3):211-215.
Leone-Bay et al., Oral delivery of sodium cromolyn: Preliminary studies In Vivo and In Vitro. Pharmaceutical Research, 13(2):222(1995).
Lindstrom et al. A Simple Pharmacokinetic Method to Evaluate the Pulmonary Dose in Clinical Practice—Analyses of Inhaled Sodium Cromoglycate. Respiratory Med ice. 98(1 ):9-16 (2004).
Luque Carla A. et al., "Treatment of ACE Inhibitor-Induced Cough", Pharmacotherapy: The Journal of Human Pharmacology and Drug Therapy, (1999), 19(7):804-810.
Markopoulou et al., "Obliterative bronchiolitis: varying presentations and clinicopathological correlation," Eur. Respur. J., 2002, 19:20-30.
Mazzone, "Old drug, new tricks: reducing cough in IPF," Lancet Respir Med, 2017, pp. 1-2.

(56) References Cited

OTHER PUBLICATIONS

Meltzer, Eric B., and Paul W. Noble., "Idiopathic pulmonary fibrosis." Orphanet journal of rare diseases 3.1 (2008): (15 pages).
Miller et al., Histone deacetylase inhibitors. Journal of Medicinal Chemistry. 46(24):5097 (2003).
Miyatake, et al., "The New Role of Disodium Cromoglycate in the Treatment of Adults with Bronchial Asthma," Allergol Intl., (2007), 56:231-239.
Moeller, et. al., "Efficacy of high dose inhaled DSCG on asthma control in young children," European Respiratory Society Annual Meeting (ERS), Berlin, Germany, Oct. 4-8, 2008.
Monk, K.R., "Thesis: Consequences of Mast Cell Signaling in Peripheral Nerve," University of Cincinnati, 2006, retrieved Oct. 17, 2017, downloaded from https://etd.ohiolink.edu/nws_etd/document/get/ucin1147889736/inline, (96 pages).
Moon, et al., "Quercetin Inhalation Inhibits the Asthmatic Responses by Exposure to Aerosolized-Ovalbumin in Conscious Guinea-pios," Arch Pharm Res., (2008), 31(6):771-778.
Moroni et al., Inhaled sodium cromoglycate to treat cough in advanced lung cancer patients. British Journal of Cancer, 7 4:309-311 (1996).
Morrison-Smith et al., "Observations on the safety of disodium cromoglycate in long-term use in children," Clinical Allergy, (1972), 2:143-151.
Moss et al., Distribution and metabolism of disodium cromoglycate in rats. Toxicology and Applied Pharmacology, 17:691-698 (1970).
Moss et al., Plasma levels and urinary excretion of disodium cromoglycate after inhalation by human volunteers. Toicology and Applied Pharmacology, 20:147-156 (1971).
NasalCrom FDA Label 2013, (4 pages).
Neale et al., The Pharmacokinetics of sodium cromoglycate in man after intravenous and inhalation administration. Britich Journal of Clinical Pharm., 22:373-382 (1986).
Nerbrink et al., "Inhalation and Deposition of Nebulized Sodium Cromoglycate in Two Different Particle Size Distributions in Children With Asthma," Pediatr Pulmonol., (2002), 34(5):351-360.
Nogrady. Chapter 4: Pro Drugs and Soft Drugs. In: Medicinal Chemistry: A Biochemical approach. New York: Oxford Universitry Press, p. 388-392 (1985).
Northern General Hospital, Brompton Hospital, "Sodium cromoglycate in chronic asthma," Br. Med. J., (1976), 1:361-364.
Patel et al., Plasma concentrations of sodium cromoglycate given by nebulisation and metered dose inhalers in patients with exercise-induced asthma: relationship to protective effect. Br. J. Clin. Pharmac., 21:231-233 (1986).
Patel, et al., "Dose-response study of sodium cromoglycate in exercise0induces asthma," (1982), 37:663-666.
Patel, et al., "The dose-duration effect of sodium cromoglycate in exercise-induced asthma," Clin Allergy, (1984), 14:87-91.
Patel, K. R. et al., Plasma concentrations of sodium cromoglycate given by nebulisation and metered dose inhalers in patients with exercise-induced asthma: relationship to protective effect. Br. J. Clin. Pharmac., 21:231-233 (1986).
PCT/US2015/015029 International Search Report and Written Opinion published Aug. 13, 2015 (18 pages).
PCT/US2015/015033 International Search Report and Written Opinion published Aug. 13, 2015 (15 pages).
PCT/US2016/042437 International Search Report and Written Opinion published Jan. 19, 2017 (17 pages).
PCT/US2016/045804 International Search Report and Written Opinion published Feb. 16, 2017 (8 pages).
PCT/US2016/045849 International Search Report and Written Opinion published Feb. 16, 2017 (8 pages).
Penttinen, et al., "Disodium cromoglycate can inhibit virus-induced cytopathic effects in vitro," BrMedJ., (1977), 1:182.
Picard et al., Expanding spectrum of mast cell activation disorders: Monoclonal and idiopathic mast cell activation syndromes. Clinical Therapeutics, 35(5): 548 (2013).
Pratter, "Overview of common causes of chronic cough," Chest, 2006, 129:59S-62S, Supplement.

U.S. Appl. No. 61/405,587, filed Oct. 7, 2016 (12 pages).
U.S. Appl. No. 62/417,887, filed Nov. 4, 2016 (150 pages).
U.S. Appl. No. 62/417,898, filed Nov. 4, 2016 (165 pages).
Reijonen, et al., "Anti-inflammatory Therapy Reduces Wheezing After Bronchiolitis," Arch Pediatr Adolesc Med., (1996), 150:512-517.
Riccardi, V. M., Cutaneous manifestation of neurofibromatosis: cellular interaction, Pigmentation, and mast cells, Birth Defects Org Artie Ser, 17: 129-45 (1981) (Abstract only).
Richards et al., Absorption and disposition kinetics of cromolyn sodium and the influence of inhalation technique. Journal of Pharmacology and Experimental Therapeutics, 241 (3): 1028-1032 (1987).
Richards et al., Deep inspiration increases the absorption of inhaled sodium cromoglycate. Br. J. Clin. Pharmac., 27:861-865 (1989).
Richards et al., Effect of methacholine induced bronchoconstriction on the pulmonary distribution and plasma pharmacokinetics of inhaled sodium cromoglycate in subjects with normal and hyper-reactive airways. Thorax. 43:611-616 (1988).
Richards et al., Inhalation rate of sodium cromoglycate determines plasma pharmacokinetics and protection against AMP-induced bronchoconstriction in asthma Eu.Respir. J., 1:896-901 (1988).
Richards et al., Inhaled histamine increases the rate of absorption of sodium cromoglycate from the lung. Br. J. Clin. Pharma, 33:337-341 (1992).
Robuschi, M. et al., "Attenuation of aspirin-induced bronchoconstriction by sodium cromoglycate and nedocromil sodium", American Journal of Respiratory and Critical Care Medicine, American Lung Association, New York, NY, (1997), 155(4): 1461-1464.
Rooseboom et al., Enzyme-catalyzed activation of anticancer prodrugs. Pharmacological Reviews, 56(1):53-102 (2004).
Rsc.org. (2018). Cromolyn I The Merck Index Online. [online] Available at: https://www.rsc.org/Merck-1 ndex/monograph/print/m3851 /cromolyn?q=u nauthorize [Accessed Feb. 15, 2018].
Rsc.org. (2018). Nifedipine I The Merck Index Online. [online] Available at: https://www.rsc.org/Merck-Index/monograph/print/m7883/nifedipine?q=unauthorize [Accessed Feb. 15, 2018].
Salmon et al., How much aerosol reaches the lungs of wheezy infants and toddlers? Archives • of Disease in Childhood, 65:401-403 (1990).
Saulnier et al. An efficient method for the synthesis of guanidino prod rugs. Bioorganic & Medicinal Chemistry Letters. 4(16):1985-1990 (1994).
Shenfield, et al., "Absorption of drugs by the Lung," Br. J Clin Pharmac., (1976), 3:583-589.
Silva, PhD Patricia. "Researchers Discover Potential Biomarkers for Identifying IPF Disease Progression." Pulmonary Fibrosis News, Oct. 27, 2015, (9 pages), pulmonaryfibrosisnews.com/2015/04/01 /researchers-dis cove r-pote nti al-bio markers-foridentifying-ipf-disease-progression/.
Silverman et al. Chapter 8: Prodrugs and drug delivery systems. In: The Organic Chemistry of Drug Design and Drug Action. San Diego: Academic Press, Inc. p. 352-401 (1992).
Silverman, M., "Inhaled sodium cromoglycate," Thorax, (2001), 56:585-586.
Soferman, et al., "Comparison between bronchial response to inhaled hypoosmolar and isoosmolar solutions of sodium cromoglycate after exercise challenge," Annals of Allergy, (1990), 64:143-146.
Spooner, et al., "Mast-cell stabilising agents to prevent exercise-induced bronchoconstriction," Copyright© 2009 The Cochrane Collaboration, Article first published online: Oct. 20, 2003, pp. 1-40.
Stevens, et al., "Sodium cromoglicate: an ineffective drug or meta-analysis misused?" Pharm Stat., (2007), 6:123-137.
Storms, et al., "Cromolyn Sodium: Fitting an Old Friend into Current Asthma Treatment," J. Asthma, (2005), 42:79-89.
Tang, et al., "Aerosol Growth Studies Ill.," J Aerosol Sci., (1977), 8:321-330.
Tasche, M.J.A, et al., "Inhaled disodium , cromoglycate (DSCG) as maintenance therapy in children with asthma: a systematic review." Thorax 55.11 (2000): 913-920.

(56) References Cited

OTHER PUBLICATIONS

Taylor et al., The Influence of Liposomal encapsulation on sodium cromoglycate pharmacokinetics in man. Pharmaceutical Research, 6(7):633-636 (1989).
Taylor, et al., "Estimation of equivalent pore radii of pulmonary capillary and alveolar membranes," Am J Physiocol., (1970), 218:1133-1140.
Tulic, et al., "Contribution of the Distal Lung to the Pathologic and Physiologic Changes in Asthma," Chest, (2003), 123:348S-355S.
Tullett et al., "Dose-response effect of sodium cromoglycate pressurised aerosol in exercise induced asthma," Thorax, (1985), 40:41-44.
U.S. Appl. No. 15/750,811, filed Feb. 6, 2018 (155 pages).
U.S. Appl. No. 15/887,825, filed Feb. 2, 2018 (155 pages).
U.S. Appl. No. 14/317,130, Restriction Requirement dated Aug. 5, 2015, (701.201).
U.S. Office Action for U.S. Appl. No. 14/617,130 dated May 9, 2016 (22 pages).
U.S. Office Action for U.S. Appl. No. 14/617,130 dated Jan. 11, 2017 (24 pages).
U.S. Office Action for U.S. Appl. No. 14/617,221 dated Aug. 26, 2015 (36 pages).
U.S. Office Action for U.S. Appl. No. 14/617,221 dated Jun. 16, 2016 (33 pages).
U.S. Office Action for U.S. Appl. No. 14/617,221 dated Oct. 25, 2017 (41 pages).
U.S. Office Action for U.S. Appl. No. 14/686,535 dated Jan. 5, 2016 (13 pages).
U.S. Office Action for U.S. Appl. No. 14/686,535 dated Jun. 25, 2015 (22 pages).
U.S. Office Action for U.S. Appl. No. 15/232,731 dated Mar. 23, 2017 (22 pages).
U.S. Office Action for U.S. Appl. No. 15/232,731 dated Mar. 29, 2017 (8 pages).
U.S. Office Action for U.S. Appl. No. 15/232,731 dated Nov. 15, 2016 (19 pages).
U.S. Office Action for U.S. Appl. No. 15/232,747 dated Dec. 2, 2016 (16 pages).
U.S. Office Action for U.S. Appl. No. 14/917,221, dated Aug. 19, 2016.
U.S. Appl. No. 14/617,221 Office Action dated Aug. 26, 2015.
Urbano, et al., "Review of the NAE PP 2007 Expert Panel Report (EPR-3) on Asthma Diagnosis and Treatment Guidelines," JMCP, (2008), 14(1):41-49.
US Office Action for U.S. Appl. No. 15/117,711 dated Oct. 3, 2017 (11 pages).
US Office Action for U.S. Appl. No. 15/117,711, dated Apr. 6, 2017 (12 pages).
US Office Action for U.S. Appl. No. 15/232,747 dated Jun. 21, 2017 (22 pages).
Van De Wouden et al., "Sodium Cromoglycate for Asthma in Children(Review)," Cochran Database Syst Rev., (2003), 1-48.
Van De Wouden, et al "Inhaled sodium cromoglycate for asthma in children (Review)," Cochrane Library, (2011), 3:1-69.
Vessal et al., Effect of oral cromolyn sodium on CKD-associated pruritus and serum tryptase level: a double-blind placebo-controlled study. Nephrol Dial Transplant. 25:1541-1547 (2010).
Walker, S. R. et al., The Fate of [14C]disodium Cromoglycate in Man, J. Pharm. Pharmacol., 24:525-531 (1972).
Weiner et al., "Isotonic Nebulized Disodium Cromoglycate Provides Better Protection against Methacholine- and Exercise-induced Bronchoconstriction," Am Rev Respir Dis., (1988), 137:1309-1311.
Yahav et al., Sodium cromoglycate in asthma: correlation between response and serum concentrations. Archives of Disease in Childhood. 63:592-597 (1988).
Yamazaki, et al., "The Inhibitory Effect of Disodium Cromoglycate on the Growth of Chlamydophila (Chlamydia) pneumonia in Vitro," Biol Pharm Bull., (2006), 29(4):799-800.
Yoshimi et al., Characteristics of 1,3-Bis-(2-ethoxycarbonylchromon-5-yloxy)-2-((S)-lysyloxy)propane Di hydrochloride (N-556), a Prod mg for the oral delivery of disodium cromoglycate, in absorption and excretion in rats and rabbits. J.Pharmacobio-Dyn., 15:681-686 (1992).
Yoshimi et al., Importance of hydrolysis of amino acid moiety in water-soluble prodrugs of disodium cromoglycate for increased oral bioavailability. J.Pharmacobio-Dyn., 15:339-345 (1992).
Zakynthinos, Epaminondas, and Nikolitsa Pappa. "Inflammatory biomarkers in coronary artery disease." Journal of cardiology 53.3 (2009): 317-333.
Zamora, et al., "Neurofibromatosis-associated lung disease: a case series and literature review," European Respiratory Journal, 2007, 29: 210-214.
Bhattacharya et al., "Genome-Wide Transcriptional Profiling Reveals Connective Tissue Mast Cell Accumulation in Bronchopulmonary Dysplasia," American J. of Respiratory and Critical Care Medicine, 2012, 186:349-358.
Eber et al., "Long term sequelae of bronchopulmonary dysplasia (chronic lung disease of infancy).," Thoracx, 2001, 56: 317-323.
European Supplementary Search Report in EP Appln. No. 17858908, dated Apr. 27, 2020, 7 pages.
Speer, "Pulmonary inflammation and bronchopulmonary dysplasia," J. of Perinatology, 2006, 26:S57-S67.

\* cited by examiner

METHODS OF TREATING RESPIRATORY SYNCYTIAL VIRUS INFECTIONS

CROSS REFERENCE

This application is a continuation of U.S. application Ser. No. 15/232,747, filed Aug. 9, 2016, which is a continuation of International PCT Application No. PCT/US2015/015033, filed Feb. 9, 2015, which claims the benefit of U.S. Provisional Application No. 62/105,453, filed Jan. 20, 2015; U.S. Provisional Application No. 61/978,711, filed Apr. 11, 2014; U.S. Provisional Application No. 61/971,709, filed Mar. 28, 2014; and U.S. Provisional Application No. 61/937,928, filed Feb. 10, 2014; and, all of which are incorporated by reference herein in their entireties.

BACKGROUND OF THE INVENTION

Mast cells play a key role in the inflammatory process. They are found in the perivascular spaces of most tissues and contain pro-inflammatory and vasoactive mediators, such as serine proteases, tryptase, histamine, serotonin, proteoglycans, thromboxane, prostaglandin D2, leukotriene C4, platelet-activating factor, and eosinophil chemotactic factor. When activated, mast cells rapidly release granules and various hormone mediators into the interstitium, a process referred to as degranulation. Degranulation of mast cells can be caused by physical or chemical injury, crosslinking of immunoglobulin G receptors, or by activated complement proteins.

Mast cells are involved in the pathophysiology of a number of lung diseases and conditions. Sustained release of pro-inflammatory and vasoactive mediators from mast cells in lung tissues can result in diseases and conditions such as asthma, fibrotic lung disease, interstitial lung disease, and chronic obstructive pulmonary disease. Another lung condition in which mast cells play a role in the pathophysiology is chronic cough. Mast cells have been found in the airway smooth muscle bundles of patients with chronic cough. Moreover, chronic cough also has neurological components. Afferent vagal activity of unmyelinated C-fibers, myelinated Aδ-fibers, and stimulation of prostaglandin-sensitive nerve endings have been implicated in the pathophysiology of certain forms of cough. Some lung diseases and conditions have been treated by the local delivery of active pharmaceutical agents, including mast cell stabilizers, to the lungs. However, a need exists for improved methods of treating lung diseases and conditions mediated by mast cells.

SUMMARY OF THE INVENTION

The foregoing and further needs are satisfied by embodiments of the methods disclosed herein. Specifically, disclosed herein are methods of treating lung diseases and conditions by delivering both a systemically effective amount of a mast cell stabilizer and/or a locally effective amount of a mast cell stabilizer to a patient with an inhalation device. In some embodiments of the methods disclosed herein, administration of a mast cell stabilizer with an inhalation device produces a systemically effective amount of the mast cell stabilizer and a high deposited lung dose of the mast cell stabilizer in the patient. In certain embodiments, a lung disease or condition treatable by the methods disclosed herein is selected from the group consisting of idiopathic pulmonary fibrosis, chronic idiopathic cough, pulmonary fibrosis, bronchopulmonary fibrosis, pulmonary artery hypertension, exercise-induced bronchoconstriction, hyperactive airway disorder, respiratory infections, respiratory syncytial virus infection, bronchiolitis obliterans, sarcoidosis, lung fibrosis, cystic fibrosis, chronic cough, steroid resistant pediatric asthma, bronchiectasis, radiation fibrosis, radiation pneumonitis, fibrosing mediastinitis, Birt-Hogg-Dubé syndrome, lymphangioleiomyomatosis, neurofibromatosis type I, alpha-1 antitrypsin deficiency, elastin mutations, salla disease, familial pulmonary arterial hypertension, pulmonary alveolar proteinosis, pulmonary capillary hemangiomatosis, pulmonary veno-occlusive disease, hereditary hemorrhagic telangiectasia, pulmonary alveolar microlithiasis, Kartagener syndrome, primary ciliary dyskinesia, central alveolar hypoventilation, narcolepsy, Marfan syndrome, Ehler-Danlos syndrome, ABCA3-related lung disease, SP-A-related lung disease, SP-B-related lung disease, SP-C-related lung disease, Hermansky-Pudlak syndrome, Gaucher disease, Neiman Pick C, Wegener's granulomatosis, Goodpasture syndrome, microscopic polyangiitis, polyarteritis nodosa, Churg-Strauss syndrome, cystic adenomatoid malformation, pulmonary sequestration, neuroendocrine cell hyperplasia, amyotrophic lateral sclerosis, myasthenia gravis, dermatomyositis, polymyositis, sarcoidosis, Langerhans cell histiocytosis, idiopathic pulmonary hemosiderosis, sickle cell anemia, lymphangiomatosis, and refractory chronic cough. In some embodiments of the methods disclosed herein, the lung disease or condition is not chronic obstructive pulmonary disease, allergic asthma, non-allergic asthma, wheezing, epistaxis, laryngotracheobronchitis, bronchitis, diffuse bronchiolitis, bronchiolitis obliterans, bronchiectasis, alveolitis, community acquired pneumonia, hospital acquired pneumonia, ventilator associated pneumonia, healthcare associated pneumonia, aspiration pneumonia, lipid pneumonia, eosinophilic pneumonia, chemical pneumonia, atypic pneumonia, severe acute respiratory system disease, pulmonary infection, emphysema, sarcoidosis, tuberculosis, nontuberculous mycobacterial pulmonary diseases, cystic fibrosis, idiopathic pulmonary fibrosis, pulmonary arterial hypertension, interstitial lung disease, pertussis, or graft rejection after lung transplantation. In some embodiments, the mast cell stabilizer is selected from cromolyn sodium, cromolyn lysinate, ammonium cromoglycate, magnesium cromoglycate, dihydropyridines such as nicardipine and nifedipine, lodoxamide, nedocromil, barnidipine, YC-114, elgodipine, niguldipine, ketotifen, methylxanthines, and quercetin.

In some embodiments of the methods disclosed herein, the median particle size of a mast cell stabilizer aerosol delivered with an inhalation device is between about 3 μm and about 4 μm. In some embodiments of the methods disclosed herein, the RF (≤3.3 μm) of a composition administered with an inhalation device is at least about 30% and/or the RF (≤5 μm) is at least about 65%. In some embodiments of the methods disclosed herein, the RF (≤3.3 μm) of a composition administered with an inhalation device is at least about 45% and/or the RF (≤5 μm) is at least about 75%. In some embodiments of the methods disclosed herein, a composition is administered with an inhalation device once a day. In some embodiments of the methods disclosed herein, a composition is administered with an inhalation device twice a day. In some embodiments of the methods disclosed herein, a composition is administered with an inhalation device three times a day. In some embodiments of the methods disclosed herein, a composition is administered with an inhalation device four times a day.

In some embodiments of the methods disclosed herein, the composition is administered with a dry powder inhaler, metered dose inhaler, nebulizer, or soft mist inhaler. In some embodiments of the methods disclosed herein, the composition is administered with a high efficiency nebulizer. In some embodiments wherein the composition is administered with a dry powder inhaler, the composition comprises lactose. In some embodiments wherein the composition is administered with a dry powder inhaler, the composition does not comprise lactose.

In some embodiments of the methods disclosed herein, the mast cell stabilizer is administered to a patient having a lung disease or condition with an inhalation device is cromolyn sodium. In some embodiments, a composition administered with an inhalation device comprises greater than about 2% cromolyn sodium. In some embodiments of the methods disclosed herein, the composition comprises about 4% cromolyn sodium. In some embodiments of the methods disclosed herein, a composition administered with an inhalation device comprises about 1 mg to about 120 mg of cromolyn sodium. In some embodiments of the methods disclosed herein, a composition administered with an inhalation device comprises about 5 mg to about 80 mg of cromolyn sodium. In some embodiments of the methods disclosed herein, a composition administered with an inhalation device comprises about 20 mg to about 60 mg of cromolyn sodium. In some embodiments of the methods disclosed herein, a composition administered with an inhalation device comprises about 30 mg to about 50 mg of cromolyn sodium. In some embodiments of the methods disclosed herein, a composition administered with an inhalation device comprises about 40 mg of cromolyn sodium.

In some embodiments of the methods disclosed herein wherein the mast cell stabilizer is cromolyn sodium, administration of a composition with an inhalation device produces in a human subject group an average $AUC_{(0-\infty)}$ of the cromolyn sodium greater than about 120 ng*hr/mL, an average $C_{max}$ of the cromolyn sodium greater than about 55 ng/mL, and a deposited lung dose of the cromolyn sodium greater than about 30% after administration of the composition to the patient. In some embodiments of the methods disclosed herein wherein the mast cell stabilizer is cromolyn sodium, administration of a composition with an inhalation device produces in a human subject group an average $AUC_{(0-\infty)}$ of the cromolyn sodium greater than about 200 ng*hr/mL, an average $C_{max}$ of the cromolyn sodium greater than about 80 ng/mL, and a deposited lung dose of the mast cell stabilizer greater than about 30% after administration of the composition to the patient. In some embodiments of the methods disclosed herein wherein the mast cell stabilizer is cromolyn sodium, administration of a composition with an inhalation device produces in a human subject group an average $AUC_{(0-\infty)}$ of the cromolyn sodium greater than about 330 ng*hr/mL, an average $C_{max}$ of the cromolyn sodium greater than about 150 ng/mL, and a deposited lung dose of the cromolyn sodium greater than about 30% after administration of the composition to the patient. In some embodiments of the methods disclosed herein wherein the mast cell stabilizer is cromolyn sodium, administration of a composition with an inhalation device produces in a human subject group an average $AUC_{(0-\infty)}$ of the cromolyn sodium greater than about 525 ng*hr/mL, an average $C_{max}$ of the cromolyn sodium greater than about 230 ng/mL, and a deposited lung dose of the mast cell stabilizer greater than about 30% after administration of the composition to the patient. In some embodiments of the methods disclosed herein wherein the mast cell stabilizer is cromolyn sodium and wherein a nominal dose of 40 mg of cromolyn sodium is administered with an inhalation device, administration of the composition with the inhalation device produces in a human subject group an average $AUC_{(0-\infty)}$ of the cromolyn sodium greater than about 200 ng*hr/mL, an average $C_{max}$ of the cromolyn sodium greater than about 80 ng/mL, and a deposited lung dose of the mast cell stabilizer greater than about 30% after administration of the composition to the patient. In some embodiments of the methods disclosed herein wherein the mast cell stabilizer is cromolyn sodium and wherein a nominal dose of 40 mg of cromolyn sodium is administered with an inhalation device, administration of the composition with the inhalation device produces in a human subject group an average $AUC_{(0-\infty)}$ of the cromolyn sodium greater than about 330 ng*hr/mL, an average $C_{max}$ of the cromolyn sodium greater than about 150 ng/mL, and a deposited lung dose of the cromolyn sodium greater than about 30% after administration of the composition to the patient. In some embodiments of the methods disclosed herein wherein the mast cell stabilizer is cromolyn sodium and wherein a nominal dose of 80 mg of cromolyn sodium is administered with an inhalation device, administration of the composition with the inhalation device produces in a human subject group an average $AUC_{(0-\infty)}$ of the cromolyn sodium greater than about 525 ng*hr/mL, an average $C_{max}$ of the cromolyn sodium greater than about 230 ng/mL, and a deposited lung dose of the mast cell stabilizer greater than about 30% after administration of the composition to the patient. In some embodiments wherein the mast cell stabilizer is cromolyn sodium, administration of a composition with an inhalation device produces in a human subject group an average $AUC_{(0-\infty)}$ of cromolyn sodium greater than about 120 ng*hr/mL and a deposited lung dose of the mast cell stabilizer greater than about 30%. In some embodiments wherein the mast cell stabilizer is cromolyn sodium, administration of a composition with an inhalation device produces in a human subject group an average $AUC_{(0-\infty)}$ of cromolyn sodium greater than about 200 ng*hr/mL and a deposited lung dose of the mast cell stabilizer greater than about 30%. In some embodiments wherein the mast cell stabilizer is cromolyn sodium, administration of a composition with an inhalation device produces in a human subject group an average $AUC_{(0-\infty)}$ of cromolyn sodium greater than about 330 ng*hr/mL and a deposited lung dose of the mast cell stabilizer greater than about 30%. In some embodiments wherein the mast cell stabilizer is cromolyn sodium, administration of a composition with an inhalation device produces in a human subject group an average $AUC_{(0-\infty)}$ of cromolyn sodium greater than about 525 ng*hr/mL and a deposited lung dose of the mast cell stabilizer greater than about 30%. In some embodiments wherein the mast cell stabilizer is cromolyn sodium, administration of a composition with an inhalation device produces in a human subject group an average $AUC_{(0-\infty)}$ of cromolyn sodium greater than about 120 ng*hr/mL, and the composition has an RF (≤3.3 µm) of at least about 30%. In some embodiments wherein the mast cell stabilizer is cromolyn sodium, administration of a composition with an inhalation device produces in a human subject group an average $AUC_{(0-\infty)}$ of cromolyn sodium greater than about 200 ng*hr/mL, and the composition has an RF (≤3.3 µm) of at least about 30%. In some embodiments wherein the mast cell stabilizer is cromolyn sodium, administration of a composition with an inhalation device produces in a human subject group an average $AUC_{(0-\infty)}$ of cromolyn sodium greater than about 330 ng*hr/mL, and the composition has an RF (≤3.3 µm) of at least about 40%. In some embodiments wherein the mast cell stabilizer is cromolyn sodium, administration of a composition with an inhalation device produces in a human subject group an average $AUC_{(0-\infty)}$ of cromolyn sodium greater than about 525 ng*hr/mL, and the composition has an RF (≤3.3 μm) of at least about 40%.

In some embodiments of the methods disclosed herein, a high concentration, hypotonic, room temperature stable solution formulation of cromolyn sodium is administered with a high efficiency nebulizer. In some embodiments, a composition administered with a high efficiency nebulizer is stable at room temperature for more than about two years. In some embodiments, a composition administered with a high efficiency nebulizer comprises one or more of purified water, sodium chloride, mannitol, and sodium EDTA. In some embodiments of the methods disclosed herein, a composition administered with a high efficiency nebulizer has a fill volume of about 0.1 mL to about 5 mL. In some embodiments of the methods disclosed herein, a composition administered with a high efficiency nebulizer has a fill volume of about 2 mL or less. In some embodiments of the methods disclosed herein, a composition administered with a high efficiency nebulizer has an osmolality greater than about 70 mOsm/kg. In some embodiments of the methods disclosed herein, a composition administered with a high efficiency nebulizer that emits droplets having an MMAD of about 4.1 μm or less and a GSD of about 1.7. In some embodiments of the methods disclosed herein, a composition administered with a high efficiency nebulizer that emits droplets having an MMAD of about 3.5 μm or less and a GSD of about 1.7. In some embodiments of the methods disclosed herein, a composition is administered with a high efficiency nebulizer in less than about five minutes. In some embodiments of the methods disclosed herein, a composition is administered with a high efficiency nebulizer in less than about three minutes.

DETAILED DESCRIPTION OF THE INVENTION

Unless defined otherwise, all technical and scientific terms used herein have the same meaning as commonly understood by one of skill in the art to which the inventions described herein belong. All publications, patents, and patent applications mentioned in this specification are hereby incorporated by reference to the same extent as if each individual publication, patent, or patent application was specifically and individually indicated to be incorporated by reference.

Definition of Terms

As used herein, the term "about" is used synonymously with the term "approximately." Illustratively, the use of the term "about" with regard to a certain therapeutically effective pharmaceutical dose indicates that values slightly outside the cited values, e.g., plus or minus 0.1% to 10%, are also effective and safe.

As used herein, the terms "comprising," "including," "such as," and "for example" (or "e.g.") are used in their open, non-limiting sense.

As used herein, the phrase "consisting essentially of" is a transitional phrase used in a claim to indicate that the following list of ingredients, parts or process steps must be present in the claimed composition, machine or process, but that the claim is open to unlisted ingredients, parts or process steps that do not materially affect the basic and novel properties of the invention.

"Nominal dose," as used herein, refers to the loaded dose, which is the amount of mast cell stabilizer in an inhalation device prior to administration to the patient. The volume of solution containing the nominal dose is referred to as the "fill volume."

"$AUC_{last}$" as used herein refers to the area under the curve from time zero to time of last measurable concentration of active pharmaceutical ingredient (API).

"$AUC_{last}^{HEN}$" as used herein refers to the area under a blood plasma concentration curve up to the last time point for the nominal dose of active pharmaceutical ingredient (API) administered with a high efficiency nebulizer.

"$AUC_{last}^{Conv}$" as used herein refers to the area under a blood plasma concentration curve up to the last time point for a nominal dose of active pharmaceutical ingredient (API) administered with a conventional inhalation device.

"$AUC_{(0-\infty)}$" as used herein refers to the total area under a blood plasma concentration curve for an active pharmaceutical ingredient (API).

"$AUC_{(0-\infty)}^{HEN}$" as used herein refers to the total area under a blood plasma concentration curve for a nominal dose of active pharmaceutical ingredient (API) administered with a high efficiency nebulizer.

"$AUC_{(0-\infty)}^{Conv}$" as used herein refers to the total area under a blood plasma concentration curve for a nominal dose of active pharmaceutical ingredient (API) administered with a conventional inhalation device.

$AUC_{(0-\infty)}$ can be determined by methods known to those of skill in the art. For example, the $AUC_{(0-\infty)}$ of an API can be determined by collecting blood samples from a subject at various time points after administration of an API to the subject, separating plasma from the blood samples, extracting the API from the separated plasma samples, e.g., by solid-phase extraction, quantifying the amount of the API extracted from each sample of separated plasma, e.g., by liquid chromatography-tandem mass spectrometry (LC-MS/MS), plotting the concentration of API in each sample versus the time of collection after administration, and calculating the area under the curve.

"Substantially the same nominal dose" as used herein means that a first nominal dose of an active pharmaceutical ingredient (API) contains approximately the same number of millimoles of the mast cell stabilizer as a second nominal dose of the mast cell stabilizer.

"Bioavailability" as used herein refers to the amount of unchanged API that reaches the systemic circulation, expressed as a percentage of the dosage of the API that is administered to a subject. By definition, the bioavailability of an intravenous solution containing the active pharmaceutical ingredient (API) is 100%. The bioavailability of an API can be determined by methods known to those of skill in the art. For example, the bioavailability of an API can be determined by collecting urine samples from a subject at various time points following administration of the API to the subject, extracting the API from the urine samples, e.g., by solid-phase extraction, quantifying the amount of the API in each urine sample, adjusting the amount of API collected from the urine by a factor based on the amount of API reaching systemic circulation that is excreted in the urine, and calculating the percentage of the API administered to the subject that reaches the systemic circulation of the subject. In a specific embodiment, the bioavailability of cromolyn sodium can be determined as described in Walker et al., 24 *J. Pharm. Pharmacol.* 525-31 (1972). In the case of cromolyn sodium, the amount of the compound isolated from the urine is multiplied by two to calculate the total amount reaching systemic circulation after administration because the compound is known to be excreted unmetabolized in equal parts in the urine and feces, i.e., approximately 50% of the amount of cromolyn sodium that reaches systemic circulation is excreted in the urine and approximately 50% of the amount of cromolyn sodium that reaches systemic circulation is excreted in the feces.

"Enhanced lung deposition" as used herein refers to an increase in drug deposition (deposited lung dose) arising out of, for example, improved efficiency of drug delivery.

"Deposited dose" or "deposited lung dose" is the amount of mast cell stabilizer deposited in the lung. The deposited dose or deposited lung dose may be expressed in absolute terms, for example in mg or µg of API deposited in the lungs. The deposited lung dose may also be expressed in relative terms, for example calculating the amount of API deposited as a percentage of the nominal dose.

"$C_{max}$" as used herein refers to the maximum plasma concentration for an active pharmaceutical ingredient (API).

"$C_{max}^{HEN}$" as used herein refers to the maximum blood plasma concentration for a nominal dose of the active pharmaceutical ingredient (API) administered with a high efficiency nebulizer.

"$C_{max}^{Conv}$" as used herein refers to the maximum blood plasma concentration for a nominal dose of the active pharmaceutical ingredient (API) administered with a conventional inhalation device.

$C_{max}$ can be determined by methods known to those of skill in the art. For example, the $C_{max}$ of an API can be determined by collecting blood samples from a subject at various time points after administration of an API to the subject, separating plasma from the blood samples, extracting the API from the separated plasma samples, e.g., by solid-phase extraction, quantifying the amount of the API extracted from each sample of separated plasma, e.g., by LC-MS/MS, plotting the concentration of API in each sample versus the time of collection after administration, and identifying the peak concentration of the API on the curve.

"Enhanced pharmacokinetic profile" means an improvement in some pharmacokinetic parameter. Pharmacokinetic parameters that may be improved include AUC (0-4 or 0-6 or 0-8 h), $AUC_{last}$, $AUC_{(0-\infty)}$, $T_{max}$, $T_{1/2}$, and $C_{max}$. In some embodiments, the enhanced pharmacokinetic profile may be measured quantitatively by comparing a pharmacokinetic parameter obtained for a nominal dose of an active pharmaceutical ingredient (API) administered by one route of administration, such as an inhalation device (e.g., a high efficiency nebulizer) with the same pharmacokinetic parameter obtained with the same nominal dose of active pharmaceutical ingredient (API) administered by a different route of administration, such as a different type of inhalation device or an oral formulation (e.g., oral tablet, oral capsule, or oral solution).

"Blood plasma concentration" refers to the concentration of an active pharmaceutical ingredient (API) in the plasma component of blood of a subject or patient population.

"Patient" or "subject" refers to the animal (especially mammal) or human being treated.

A "subject group" or "patient group" has a sufficient number of subjects or patients to provide a statistically significant average measurement of the relevant pharmacokinetic parameter. All members of the "subject group" or "patient group" have pharmacokinetic parameters for the mast cell stabilizers that fall within statistically normal ranges (i.e., there are no outliers), and no member is included on the basis of non-standard or unusual measurements.

"Nebulizer," as used herein, refers to a device that turns medications, compositions, formulations, suspensions, and mixtures, etc. into a fine aerosol mist for delivery to the lungs.

"Drug absorption" or simply "absorption" typically refers to the process of movement of drug from site of delivery of a drug across a barrier into a blood vessel or the site of action, e.g., a drug being absorbed via the pulmonary capillary beds of the alveoli into the systemic circulation.

"$T_{max}$" as used herein refers to the amount of time necessary for an active pharmaceutical ingredient (API) to attain maximum blood plasma concentration.

"$T_{max}^{HEN}$" as used herein refers to the amount of time necessary for a nominal dose of an active pharmaceutical ingredient (API) to attain maximum blood plasma concentration after administration with a high efficiency nebulizer.

"$T_{max}^{Conv}$" as used herein refers to the amount of time necessary for a nominal dose of an active pharmaceutical ingredient (API) to attain maximum blood plasma concentration after administration with a conventional inhalation device.

The term "treat" and its grammatical variants (e.g., "to treat," "treating," and "treatment") refer to administration of an active pharmaceutical ingredient to a patient with the purpose of ameliorating or reducing the incidence of one or more symptoms of a condition or disease state in the patient. Such symptoms may be chronic or acute; and such amelioration may be partial or complete. In the present context, treatment entails administering a mast cell stabilizer to a patient via any route of administration disclosed herein.

As used herein, the term "high concentration" refers to a concentration greater than 1% by weight. For example, in a specific embodiment, a "high concentration" formulation of cromolyn sodium comprises cromolyn sodium at a concentration of greater than 1% by weight.

As used herein, the term "hypotonic" refers to a formulation that has a tonicity less than 295 mOsm/kg.

The term "prophylaxis" refers to administration of an active pharmaceutical ingredient to a patient with the purpose of reducing the occurrence or recurrence of one or more acute symptoms associated with a disease state or a condition in the patient. In the present context, prophylaxis entails administering a mast cell stabilizer to a patient via any route of administration disclosed herein. Thus, prophylaxis includes reduction in the occurrence or recurrence rate of a lung disease or condition. However, prophylaxis is not intended to include complete prevention of onset of a disease state or a condition in a patient who has not previously been identified as suffering from the disease or the condition.

As used herein, a "systemically effective amount" is an amount of mast cell stabilizer in the body of a patient as a whole that is effective for the treatment or prophylaxis of a lung disease or condition. A "systemically effective amount" may be expressed, for example, as the mass of a mast cell stabilizer, or concentration of a mast cell stabilizer, in a patient's plasma. A "systemically effective amount" may differ depending on the specific mast cell stabilizer and the specific lung disease or condition.

As used herein, a "locally effective amount" is an amount of mast cell stabilizer in a particular region of the body of a patient, namely the lungs of a patient, that is effective for the treatment or prophylaxis of a lung disease or condition. A "locally effective amount" may be expressed, for example, as the mass of a mast cell stabilizer, or concentration of a mast cell stabilizer, in a patient's lung tissue. A "locally effective amount" may differ depending on the specific mast cell stabilizer and the specific lung disease or condition.

As used herein, a difference is "significant" if a person skilled in the art would recognize that the difference is probably real. In some embodiments, significance may be determined statistically, in which case two measured parameters may be referred to as statistically significant. In some embodiments, statistical significance may be quantified in terms of a stated confidence interval (CI), e.g., greater than 90%, greater than 95%, greater than 98%, etc. In some embodiments, statistical significance may be quantified in terms of a p value, e.g., less than 0.5, less than 0.1, less than 0.05, etc. The person skilled in the art will recognize these expressions of significance and will know how to apply them appropriately to the specific parameters that are being compared.

Methods of Treating Lung Diseases and Conditions with Mast Cell Stabilizers

Disclosed herein are methods for the treatment or prophylaxis of a lung disease or condition comprising administering a composition comprising one or more mast cell stabilizers with an inhalation device. In some embodiments of the methods disclosed herein, administration of a composition comprising a mast cell stabilizer to a patient with an inhalation device produces both a systemically effective amount of the mast cell stabilizer and a locally effective amount of the mast cell stabilizer to treat a lung disease or condition. In some embodiments of the methods disclosed herein, administration of a mast cell stabilizer to a patient with an inhalation device produces a systemically effective amount of the mast cell stabilizer and a high deposited lung dose of the mast cell stabilizer in the patient to treat a lung disease or condition. In some embodiments of the methods disclosed herein, administration of a mast cell stabilizer to a patient with an inhalation device produces a systemically effective amount of the mast cell stabilizer, a locally effective amount of the mast cell stabilizer, and a high deposited lung dose of the mast cell stabilizer in the patient to treat a lung disease or condition. Thus, in some embodiments of the methods disclosed herein, administration of a mast cell stabilizer with an inhalation device provides improved efficacy for the treatment of a lung disease or condition by producing both a systemically effective amount of the mast cell stabilizer and a locally effective amount of the mast cell stabilizer. In some embodiments of the methods disclosed herein, administration of a mast cell stabilizer with an inhalation device provides improved efficacy for the treatment of a lung disease or condition by producing both a systemically effective amount of the mast cell stabilizer and a high deposited lung dose of the mast cell stabilizer. In some embodiments of the methods disclosed herein, administration of a mast cell stabilizer with an inhalation device provides improved efficacy for the treatment of a lung disease or condition by producing a systemically effective amount of the mast cell stabilizer, a locally effective amount of the mast cell stabilizer, and a high deposited lung dose of the mast cell stabilizer.

Lung diseases or conditions treatable by the methods disclosed herein include, but are not limited to, idiopathic pulmonary fibrosis, chronic idiopathic cough, pulmonary fibrosis, bronchopulmonary fibrosis, pulmonary artery hypertension, exercise-induced bronchoconstriction, hyperactive airway disorder, respiratory infections, respiratory syncytial virus infection, bronchiolitis obliterans, sarcoidosis, lung fibrosis, cystic fibrosis, chronic cough, steroid resistant pediatric asthma, bronchiectasis, radiation fibrosis, radiation pneumonitis, fibrosing mediastinitis, Birt-Hogg-Dubé syndrome, lymphangioleiomyomatosis, neurofibromatosis type I, alpha-1 antitrypsin deficiency, elastin mutations, salla disease, familial pulmonary arterial hypertension, pulmonary alveolar proteinosis, pulmonary capillary hemangiomatosis, pulmonary veno-occlusive disease, hereditary hemorrhagic telangiectasia, pulmonary alveolar microlithiasis, Kartagener syndrome, primary ciliary dyskinesia, central alveolar hypoventilation, narcolepsy, Marfan syndrome, Ehler-Danlos syndrome, ABCA3-related lung disease, SP-A-related lung disease, SP-B-related lung disease, SP-C-related lung disease, Hermansky-Pudlak syndrome, Gaucher disease, Neiman Pick C, Wegener's granulomatosis, Goodpasture syndrome, microscopic polyangiitis, polyarteritis nodosa, Churg-Strauss syndrome, cystic adenomatoid malformation, pulmonary sequestration, neuroendocrine cell hyperplasia, amyotrophic lateral sclerosis, myasthenia gravis, dermatomyositis, polymyositis, sarcoidosis, Langerhans cell histiocytosis, idiopathic pulmonary hemosiderosis, sickle cell anemia, lymphangiomatosis, and refractory chronic cough. In some embodiments of the methods disclosed herein, the lung disease or condition is not chronic obstructive pulmonary disease, allergic asthma, non-allergic asthma, or wheezing. In some embodiments of the methods disclosed herein, the lung disease or condition is not epistaxis, laryngotracheobronchitis, bronchitis, diffuse bronchiolitis, bronchiolitis obliterans, bronchiectasis, alveolitis, community acquired pneumonia, hospital acquired pneumonia, ventilator associated pneumonia, healthcare associated pneumonia, aspiration pneumonia, lipid pneumonia, eosinophilic pneumonia, chemical pneumonia, atypic pneumonia, severe acute respiratory system disease, pulmonary infection, emphysema, sarcoidosis, tuberculosis, non-tuberculous mycobacterial pulmonary diseases, cystic fibrosis, idiopathic pulmonary fibrosis, pulmonary arterial hypertension, interstitial lung disease, pertussis, or graft rejection after lung transplantation.

As used herein, a "mast cell stabilizer" refers to an agent that inhibits degranulation and/or the release of pro-inflammatory and vasoactive mediators from mast cells. Mast cell stabilizers include, but are not limited to, cromolyn, dihydropyridines such as nicardipine and nifedipine, lodoxamide, nedocromil, barnidipine, YC-114, elgodipine, niguldipine, ketotifen, methylxanthines, quercetin, and pharmaceutically salts thereof. In some embodiments, the mast cell stabilizer is a pharmaceutically acceptable salt of cromolyn, such as cromolyn sodium, cromolyn lysinate, ammonium cromonglycate, and magnesium cromoglycate. In some embodiments, mast cell stabilizers include but are not limited to compounds disclosed in U.S. Pat. Nos. 6,207,684; 4,634,699; 6,207,684; 4,871,865; 4,923,892; 6,225,327; 7,060,827; 8,470,805; 5,618,842; 5,552,436; 5,576,346; 8,252,807; 8,088,935; 8,617,517; 4,268,519; 4,189,571; 3,790,580; 3,720,690; 3,777,033; 4,067,992; 4,152,448; 3,419,578; 4,847,286; 3,683,320; and 4,362,742; U.S. Patent Application Publication Nos. 2011/112183 and 2014/140927; European Patent Nos. 2391618; 0163683; 0413583; and 0304802; International Patent Application Nos. WO2010/042504; WO85/02541; WO2014/115098; WO2005/063732; WO2009/131695; and WO2010/088455; all of which are incorporated by reference. Mast cell stabilizers, including cromolyn and pharmaceutically acceptable salts, prodrugs, and adducts thereof, may be prepared by methods known in the art.

In some embodiments, mast cell stabilizers described herein may be prepared as prodrugs. A "prodrug" refers to an agent that is converted into the parent drug in vivo. The prodrug can be designed to alter the metabolic stability or the transport characteristics of a drug, to mask side effects or toxicity, to improve the flavor of a drug, or to alter other characteristics or properties of a drug. In some embodiments, the prodrug has improved bioavailability relative to the parent drug. In some embodiments, the prodrug has improved solubility in pharmaceutical compositions over the parent drug. In some embodiments, prodrugs may be designed as reversible drug derivatives, for use as modifiers to enhance drug transport to site-specific tissues. In some embodiments, a prodrug of a mast cell stabilizer is an ester of the mast cell stabilizer, which is hydrolyzed to the carboxylic acid, the parent mast cell stabilizer. In some embodiments, a prodrug comprises a short peptide (polyaminoacid) bonded to an acid group, wherein the peptide is metabolized in vivo to reveal the parent drug. In certain embodiments, upon in vivo administration, a prodrug is chemically converted to the biologically, pharmaceutically or therapeutically active form of the mast cell stabilizer. In certain embodiments, a prodrug is enzymatically metabolized by one or more steps or processes to the parent mast cell stabilizer. In certain embodiments, the mast cell stabilizer is a prodrug of cromolyn. In a specific embodiment, the prodrug of cromolyn is cromoglicate lisetil.

To produce a prodrug, a pharmaceutically active mast cell stabilizer compound is modified such that the active compound will be regenerated upon in vivo administration. In some embodiments, prodrugs of mast cell stabilizers are designed by virtue of knowledge of pharmacodynamic processes and drug metabolism in vivo. See, e.g., Nogrady (1985) *Medicinal Chemistry A Biochemical Approach*, Oxford University Press, New York, pages 388-392; Silverman (1992), The Organic Chemistry of Drug Design and Drug Action, Academic Press, Inc., San Diego, pages 352-401, Saulnier et al., (1994), *Bioorganic and Medicinal Chemistry Letters*, Vol. 4, p. 1985; Rooseboom et al., *Pharmacological Reviews*, 56:53-102, 2004; Miller et al., *J. Med. Chem.* Vol. 46, no. 24, 5097-5116, 2003; Aesop Cho, "Recent Advances in Oral Prodrug Discovery", *Annual Reports in Medicinal Chemistry*, Vol. 41, 395-407, 2006.

In some embodiments, mast cell stabilizers described herein include isotopically-labeled compounds, which are identical to those recited herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, fluorine and chlorine, such as, for example, $^2H$, $^3H$, $^{13}C$, $^{14}C$, $^{15}N$, $^{18}O$, $^{17}O$, $^{35}S$, $^{18}F$, $^{36}Cl$, respectively. Certain isotopically labeled compounds described herein, for example those with isotopes such as deuterium, i.e., $^2H$, can afford certain therapeutic advantages resulting from greater metabolic stability, such as, for example, increased in vivo half-life or reduced dosage requirements. In certain embodiments, the mast cell stabilizer is isotopically labeled cromolyn, or a pharmaceutically acceptable salt thereof, such as cromolyn sodium. In some embodiments, the mast cell stabilizer is deuterium-labeled cromolyn sodium.

In some embodiments, mast cell stabilizers described herein may be pegylated, wherein one or more polyethylene glycol (PEG) polymers are covalently attached to the mast cell stabilizers. In some embodiments, pegylated mast cell stabilizers increase the half-life of the mast cell stabilizers in the body. In some embodiments, pegylation of the mast cell stabilizers increases the hydrodynamic size of the mast cell stabilizers and reduces their renal clearance. In some embodiments, pegylation of the mast cell stabilizers increases the solubility of the mast cell stabilizers. In some embodiments, pegylation of the mast cell stabilizers protects the mast cell stabilizers from proteolytic degradation.

Mast cell stabilizers may be administered in the methods disclosed herein in a suitable dose or nominal dose as determined by one of ordinary skill in the art. In some embodiments, the mast cell stabilizer is administered at a dosage or nominal dosage of less than about 1 mg/dose, about 1 mg/dose to about 100 mg/dose, about 1 mg/dose to about 120 mg/dose, about 5 mg/dose to about 80 mg/dose, about 20 mg/dose to about 60 mg/dose, about 30 mg/dose to about 50 mg/dose, or greater than about 100 mg/dose. In some embodiments, the mast cell stabilizer is administered in less than about 1 mg, about 1 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg doses, about 135 mg, about 140 mg, about 145 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, or about 1000 mg doses.

In some embodiments of the methods disclosed herein, cromolyn sodium is administered at a dosage or nominal dosage of less than about 1 mg/dose, about 1 mg/dose to about 100 mg/dose, about 1 mg/dose to about 120 mg/dose, about 5 mg/dose to about 80 mg/dose, about 20 mg/dose to about 60 mg/dose, or about 30 mg/dose to about 50 mg/dose, or greater than about 100 mg/dose. In other embodiments, cromolyn sodium is administered in less than about 1 mg, about 1 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg doses, about 135 mg, about 140 mg, about 145 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, or about 1000 mg doses.

In some embodiments of the methods disclosed herein, further active agents other than a mast cell stabilizer that are effective for the treatment or prophylaxis of a lung disease or condition are administered or co-administered with the mast cell stabilizer. Such further active agents may be administered separately, or may be incorporated into a composition comprising a mast cell stabilizer. Such further active agents include, but are not limited to, leukotriene antagonists, steroidal and non-steroidal anti-inflammatory drugs, anti-allergics, β-agonists, anticolinergics, corticosteroids, testosterone derivatives, phosphodiesterase inhibitors, endothelin antagonists, mucolytics, antibiotics, antifungals, antivirals, antioxidants, vitamins, heparinoids, α-antitrypsin, lung surfactants, anti-inflammatory compounds, glucocorticoids, anti-infective agents, antibiotics, antifungals, antivirals, antiseptics, vasoconstrictors, vasodilators, wound healing agents, local anesthetics, peptides, and proteins.

Anti-inflammatory compounds which may be administered or co-administered with a mast cell stabilizer in the methods disclosed herein include but are not limited to betamethasone, beclomethasone, budesonide, ciclesonide, dexamethasone, desoxymethasone, fluoconolone acetonide, flucinonide, flunisolide, fluticasone, icomethasone, rofleponide, triamcinolone acetonide, fluocortin butyl, hydrocortisone, hydroxycortisone-17-butyrate, prednicarbate, 6-methylprednisolone aceponate, mometasone furoate, elastane-, prostaglandin-, leukotriene, bradykinin-antagonists, non-steroidal anti-inflammatory drugs (NSAIDs), such as ibuprofen and indometacin.

Anti-allergic agents which may be administered or co-administered with a mast cell stabilizer in the methods disclosed herein include but are not limited to glucocorticoids, nedocromil, cetirizine, loratidine, montelukast, roflumilast, ziluton, omalizumab, heparins and heparinoids and other antihistamines, azelastine, cetirizine, desloratadine, ebastine, fexofenadine, levocetirizine, loratadine.

Anti-infective agents which may be administered or co-administered with a mast cell stabilizer in the methods disclosed herein include but are not limited to benzylpenicillins (penicillin-G-sodium, clemizone penicillin, benzathine penicillin G), phenoxypenicillins (penicillin V, propicillin), aminobenzylpenicillins (ampicillin, amoxycillin, bacampicillin), acylaminopenicillins (azlocillin, mezlocillin, piperacillin, apalcillin), carboxypenicillins (carbenicillin, ticarcillin, temocillin), isoxazolyl penicillins (oxacillin, cloxacillin, dicloxacillin, flucloxacillin), and amidine penicillins (mecillinam); cephalosporins, including cefazolins (cefazolin, cefazedone); cefuroximes (cefuroxime, cefamandole, cefotiam), cefoxitins (cefoxitin, cefotetan, latamoxef, flomoxef), cefotaximes (cefotaxime, ceftriaxone, ceftizoxime, cefinenoxime), ceftazidimes (ceftazidime, cefpirome, cefepime), cefalexins (cefalexin, cefaclor, cefadroxil, cefradine, loracarbef, cefprozil), and cefiximes (cefixime, cefpodoxim proxetile, cefuroxime axetil, cefetamet pivoxil, cefotiam hexetil), loracarbef, cefepim, clavulanic acid/amoxicillin, ceftobiprole; synergists, including beta-lactamase inhibitors, such as clavulanic acid, sulbactam, and tazobactam; carbapenems, including imipenem, cilastin, meropenem, doripenem, tebipenem, ertapenem, ritipenam, and biapenem; monobactams, including aztreonam; aminoglycosides, such as apramycin, gentamicin, amikacin, isepamicin, arbekacin, tobramycin, netilmicin, spectinomycin, streptomycin, capreomycin, neomycin, paromoycin, and kanamycin; macrolides, including erythromycin, clarythromycin, roxithromycin, azithromycin, dithromycin, josamycin, spiramycin and telithromycin; gyrase inhibitors or fluoroquinolones, including ciprofloxacin, gatifloxacin, norfloxacin, ofloxacin, levofloxacin, perfloxacin, lomefloxacin, fleroxacin, garenoxacin, clinafloxacin, sitafloxacin, prulifloxacin, olamufloxacin, caderofloxacin, gemifloxacin, balofloxacin, trovafloxacin, and moxifloxacin; tetracyclins, including tetracyclin, oxytetracyclin, rolitetracyclin, minocyclin, doxycycline, tigecycline and aminocycline; glycopeptides, including vancomycin, teicoplanin, ristocetin, avoparcin, oritavancin, ramoplanin, and peptide 4; polypeptides, including plectasin, dalbavancin, daptomycin, oritavancin, ramoplanin, dalbavancin, telavancin, bacitracin, tyrothricin, neomycin, kanamycin, mupirocin, paromomycin, polymyxin B and colistin; sulfonamides, including sulfadiazine, sulfamethoxazole, sulfalene, co-trimoxazole, co-trimetrol, co-trimoxazine, and co-tetraxazine; azoles, including clotrimazole, oxiconazole, miconazole, ketoconazole, itraconazole, fluconazole, metronidazole, tinidazole, bifonazole, ravuconazole, posaconazole, voriconazole, and ornidazole and other antifungals including flucytosin, griseofluvin, tonoftal, naftifine, terbinafine, amorolfine, ciclopiroxolamin, echinocandins, such as micafungin, caspofungin, anidulafungin; nitrofurans, including nitrofurantoin and nitrofuranzone; polyenes, including amphotericin B, natamycin, nystatin, flucocytosine; other antibiotics, including tithromycin, lincomycin, clindamycin, oxazolidinones (linezolids), ranbezolid, streptogramine A+B, pristinamycin A+B, virginiamycin A+B, dalfopristin/quinupristin (Synercid), chloramphenicol, ethambutol, pyrazinamide, terizidon, dapson, prothionamide, fosfomycin, fucidinic acid, rifampicine, isoniazid, cycloserine, terizidone, ansamycin, lysostaphin, iclaprim, mirocin B17, clerocidin, filgrastim, and pentamidine; antivirals, including aciclovir, ganciclovir, birivudine, valaciclovir, zidovudine, didanosine, thiacytidin, stavudine, lamivudine, zalcitabine, ribavirin, nevirapirine, delaviridine, trifluridine, ritonavir, saquinavir, indinavir, foscarnet, amantadine, podophyllotoxin, vidarabine, tromantadine, and proteinase inhibitors; plant extracts or ingredients, such as plant extracts from chamomile, hamamelis, echinacea, calendula, papain, pelargonium, essential oils, myrtol, pinen, limonen, cineole, thymol, mentol, tee tree oil, alpha-hederin, bisabolol, lycopodin, vitapherole; wound healing compounds including dexpantenol, allantoin, vitamins, hyaluronic acid, alpha-antitrypsin, inorganic and organic zinc salts/compounds, interferones (alpha, beta, gamma), tumor necrosis factors, cytokines, interleukins.

Mucolytics which may be administered or co-administered with a mast cell stabilizer in the methods disclosed herein include but are not limited to DNase, P2Y2-agonists (denufosol), heparinoids, guaifenesin, acetylcysteine, carbocysteine, ambroxol, bromhexine, lecithins, myrtol, and recombinant surfactant proteins.

Local anesthetic agents which may be administered or co-administered with a mast cell stabilizer in the methods disclosed herein include but are not limited to benzocaine, tetracaine, procaine, lidocaine and bupivacaine.

Peptides and proteins which may be administered or co-administered with a mast cell stabilizer in the methods disclosed herein include but are not limited to antibodies against toxins produced by microorganisms, antimicrobial peptides such as cecropins, defensins, thionins, and cathelicidins.

Immunomodulators which may be administered or co-administered with a mast cell stabilizer in the methods disclosed herein include but are not limited to methotrexate, azathioprine, cyclosporine A, tacrolimus, sirolimus, rapamycin, mycophenolate, mofetil, cytostatics and metastasis inhibitors, alkylants, such as nimustine, melphanlane, carmustine, lomustine, cyclophosphamide, ifosfamide, trofosfamide, chlorambucil, busulfane, treosulfane, prednimustine, thiotepa; antimetabolites, e.g. cytarabine, fluorouracil, methotrexate, mercaptopurine, tioguanine; alkaloids, such as vinblastine, vincristine, vindesine; antibiotics, such as alcarubicine, bleomycine, dactinomycine, daunorubicine, doxorubicine, epirubicine, idarubicine, mitomycine, plicamycine; complexes of secondary group elements (e.g., Ti, Zr, V, Nb, Ta, Mo, W, Pt) such as carboplatinum, cis-platinum and metallocene compounds such as titanocendichloride; amsacrine, dacarbazine, estramustine, etoposide, beraprost, hydroxycarbamide, mitoxanthrone, procarbazine, temiposide; paclitaxel, iressa, zactima, poly-ADP-ribose-polymerase (PRAP) enzyme inhibitors, banoxantrone, gemcitabine, pemetrexed, bevacizumab, ranibizumab.

Proteinase inhibitors which may be administered or co-administered with a mast cell stabilizer in the methods disclosed herein include but are not limited to alpha-antitrypsin; antioxidants, such as tocopherols, glutathion; pituitary hormones, hypothalamic hormones, regulatory peptides and their inhibiting agents, corticotropine, tetracosactide, choriogonandotropine, urofolitropine, urogonadotropine, somatotropine, metergoline, desmopressine, oxytocine, argipressine, ornipressine, leuproreline, triptoreline, gonadoreline, busereline, nafareline, goselerine, somatostatine; parathyroid gland hormones, calcium metabolism regulators, dihydrotachysterole, calcitonine, clodronic acid, etidronic acid; thyroid gland therapeutics; sex hormones and their inhibiting agents, anabolics, androgens, estrogens, gestagenes, antiestrogenes; anti-migraine drugs, such as proxibarbal, lisuride, methysergide, dihydroergotamine, ergotamine, clonidine, pizotifene; hypnotics, sedatives, benzodiazepines, barbiturates, cyclopyrrolones, imidazopyridines, antiepileptics, zolpidem, barbiturates, phenyloin, primidone, mesuximide, ethosuximide, sultiam, carbamazepin, valproic acid, vigabatrine; antiparkinson drugs, such as levodopa, carbidopa, benserazide, selegiline, bromocriptine, amantadine, tiapride; antiemetics, such as thiethylperazine, bromopride, domperidone, granisetrone, ondasetrone, tropisetrone, pyridoxine; analgesics, such as buprenorphine, fentanyl, morphine, codeine, hydromorphone, methadone; fenpipramide, fentanyl, piritramide, pentazocine, buprenorphine, nalbuphine, tilidine; drugs for narcosis, such as N-methylated barbiturates, thiobarbiturates, ketamine, etomidate, propofol, benzodiazepines, droperidol, haloperidol, alfentanyl, sulfentanyl; antirheumatism drugs including tumor necrosis factor-alfa, nonsteroidal antiinflammatory drugs; antidiabetic drugs, such as insulin, sulfonylurea derivatives, biguanids, glitizols, glucagon, diazoxid; cytokines, such as interleukines, interferones, tumor necrosis factor (TNF), colony stimulating factors (GM-CSF, G-CSF, M-CSF); proteins, e.g. epoetine, and peptides, e.g. parathyrin, somatomedin C; heparine, heparinoids, urokinases, streptokinases, ATP-ase, prostacycline, sexual stimulants, and genetic material.

Inhalation Therapy

An "inhalation device," as used herein, refers to any device that is capable of administering a drug formulation to the respiratory airways of a patient. Inhalation devices include conventional inhalation devices such as metered dose inhalers (MDIs), dry powder inhalers (DPIs), jet nebulizers, ultrasonic wave nebulizers, heat vaporizers, and soft mist inhalers. Inhalation devices also include high efficiency nebulizers. Nebulizers, metered dose inhalers, and soft mist inhalers deliver pharmaceuticals by forming an aerosol which includes droplet sizes that can easily be inhaled. The aerosol can be used by a patient within the bounds of an inhalation therapy, whereby the mast cell stabilizer reaches the patient's respiratory tract upon inhalation. In some embodiments, the methods disclosed herein comprise administering to a patient a nominal dose of a mast cell stabilizer by an inhalation device. In some embodiments of the methods disclosed herein, an inhalation device is not a bronchoscope.

In some embodiments of the methods disclosed herein, administration of a composition comprising a mast cell stabilizer, e.g., cromolyn sodium, to a patient with an inhalation device, e.g., a high efficiency nebulizer, a dry powder inhaler, a metered dose inhaler, a thermal aerosol inhaler, or an electrohydrodynamic-based solution misting inhaler, is effective for the treatment or prophylaxis of a lung disease or condition because both a systemically effective amount of the mast cell stabilizer and a high deposited lung dose of the mast cell stabilizer are achieved in the patient. Thus, in some embodiments of the methods disclosed herein, administration of a composition comprising a mast cell stabilizer, e.g., cromolyn sodium, to a patient with an inhalation device, e.g., a high efficiency nebulizer, a dry powder inhaler, a metered dose inhaler, a thermal aerosol inhaler, or an electrohydrodynamic-based solution misting inhaler, is effective for the treatment or prophylaxis of a lung disease or condition that is not believed to be susceptible to treatment or prophylaxis with a mast cell stabilizer because both a systemically effective amount of the mast cell stabilizer and a high deposited lung dose of the mast cell stabilizer are achieved in the patient.

In some embodiments of the methods disclosed herein, administration of a composition comprising a mast cell stabilizer, e.g., cromolyn sodium, to a patient with an inhalation device, e.g., a high efficiency nebulizer, a dry powder inhaler, a metered dose inhaler, a thermal aerosol inhaler, or an electrohydrodynamic-based solution misting inhaler, is effective for the treatment or prophylaxis of a lung disease or condition because both a systemically effective amount of the mast cell stabilizer and a locally effective amount of the mast cell stabilizer is achieved in the patient. Thus, in some embodiments of the methods disclosed herein, administration of a composition comprising a mast cell stabilizer, e.g., cromolyn sodium, to a patient with an inhalation device, e.g., a high efficiency nebulizer, a dry powder inhaler, a metered dose inhaler, a thermal aerosol inhaler, or an electrohydrodynamic-based solution misting inhaler, is effective for the treatment or prophylaxis of a lung disease or condition that is not believed to be susceptible to treatment or prophylaxis with a mast cell stabilizer because both a systemically effective amount of the mast cell stabilizer and a locally effective amount of the mast cell stabilizer is achieved in the patient. Furthermore, in some embodiments where a mast cell stabilizer is administered with an inhalation device, e.g., a high efficiency nebulizer, the methods disclosed herein provide improved efficacy for the treatment or prophylaxis of a lung disease or condition relative to administration of a systemically effective amount of the mast cell stabilizer by a different route of administration, e.g., parenterally or orally, because administration of the mast cell stabilizer with an inhalation device, e.g., a high efficiency nebulizer, a dry powder inhaler, a metered dose inhaler, a thermal aerosol inhaler, or an electrohydrodynamic-based solution misting inhaler, provides both a systemically effective amount of the mast cell stabilizer and a locally effective amount of the mast cell stabilizer. In some embodiments, a systemically effective amount and a locally effective amount of a mast cell stabilizer is achieved by delivering the mast cell stabilizer in an aerosol generated by a vibrating mesh nebulizer that produces droplets with a MMD of 3.0-4.0 μm and a GSD of 1.5-1.8. In some embodiments of the methods disclosed herein, an aerosol is administered through a mouthpiece of a nebulizer using normal tidal breathing.

Characterization of Inhalation Devices

The efficiency of a particular inhalation device can be characterized in many different ways, including by pharmacokinetic properties, lung deposition (deposited lung dose), respirable dose (RD), delivered dose (DD), respirable fraction (RF), respirable drug delivery rate (RDDR), volumetric or mass median diameter (VIVID or MMD), mass median aerodynamic diameter (MMAD) in combination with the geometric standard deviation (GSD), and total output rate (TOR), among others. The MMAD and GSD can be measured using a cascade impactor as described in United States Phamacopeia (USP<1601>). The DD can be measured by using breath simulation apparatus as described in USP<1601>. The RF is derived from measuring the amount of drug deposited on the cascade impactor plates with a particular cut-off particle size, and expressing that as a fraction of the total amount deposited on the cascade impactor plates, the induction port and the filter. The RD is calculated by multiplying the DD by the RF. The TOR is measured by the difference in weight of the nebulizer before and after completion of nebulization divided by the duration of nebulization. VMD or MMD can be measured with a standard laser light scattering apparatus such as the Malvern Spraytec.

Pharmacokinetics is concerned with the uptake, distribution, metabolism and excretion of a drug substance. A pharmacokinetic profile comprises one or more biological measurements designed to measure the absorption, distribution, metabolism and excretion of a drug substance. One way of visualizing a pharmacokinetic profile is by means of a blood plasma concentration curve, which is a graph depicting mean active ingredient blood plasma concentration on the Y-axis and time (usually in hours) on the X-axis. Some pharmacokinetic parameters that may be visualized by means of a blood plasma concentration curve include $AUC_{last}$, $AUC_{(0-\infty)}$, $C_{max}$, $T_{1/2}$, and $T_{max}$. An enhanced pharmacokinetic profile in a patient can be indicated by increased $AUC_{last}$, $AUC_{(0-\infty)}$, $C_{max}$, or $T_{1/2}$, a decreased $T_{max}$, or an increased $T_{max}$. Enhanced levels of a mast cell stabilizer in the blood plasma of a patient may result in better control of or improved symptoms of a lung disease or condition.

The deposited lung dose may be expressed as a percentage of the nominal dose that is deposited in the lung. For example, a lung deposition of 30% means 30% of the nominal dose is deposited in the lung. Likewise, a lung deposition of 60% means 60% of the nominal dose is deposited in the lung, and so forth. Lung deposition (deposited lung dose) can be determined using methods of scintigraphy or deconvolution.

RF, DD, RD, and RDDR are calculated parameters based on in vitro data that provide technical dimensions for the efficiency of an inhalation device. RF represents the percentage of the delivered aerosol, or inhaled mass, that penetrates into the gas-exchange region of the lungs. RF may be measured with a cascade impactor or laser diffraction apparatus. RF is expressed herein as the percentage of an aerosol delivered with an inhalation device that has a particular particle diameter or range of particle diameters. For example, the term "RF (≤3.3 μm)" as used herein refers to the percentage of an aerosol delivered with an inhalation device that has a particle diameter less than or equal to 3.3 μm. Similarly, the terms "RF (1-5 μm)" and "RF (≤5 μm)" as used herein refers to the percentage of an aerosol delivered with an inhalation device that has a particle diameter in the range of 1 μm to 5 μm, or less than 5 μm, respectively. DD is the portion of the nominal dose that is actually emitted from the mouthpiece of the device. The difference between the nominal dose and the DD is the amount of drug lost primarily as residues, i.e., the amount of drug remaining in the inhalation device after administration or lost in aerosol form. RD is an expression of the delivered mass of drug contained within droplets or particles having a certain diameter emitted from an inhalation device, such as a DPI, MDI, or nebulizer that, are small enough to penetrate into the lung of a patient. The RD is determined by multiplying the DD by the RF. RDDR is the speed at which a respirable dose of the drug is delivered to a patient's lungs. RDDR, measured as a function of μg or mg/min, is determined by dividing the RD by the amount of time necessary for inhalation. The amount of time necessary for inhalation is measured as the amount of time from the first moment of administration of the emitted droplet or powder from the nebulizer, DPI, or MDI until the emitted or delivered droplet or powder of a respirable diameter is delivered to the lung.

Aerosol particle/droplet size is one factor determining the deposition of aerosol drugs in the airways. The distribution of aerosol particle/droplet size can be expressed in terms of one or more of VMD/MMAD and GSD. GSD is a dimensionless measure of a droplet size distribution curve relevant for characterizing terms such as VMD, MMD, and MMAD. In general, the smaller the GSD for a particular particle size distribution, the narrower the distribution curve.

Conventional Inhalation Devices

Conventional inhalation devices may be mechanical or electrical, and include, for example, jet nebulizers and ultrasonic nebulizers. Jet nebulizers generally utilize compressors to generate compressed air, which breaks the liquid medication into small breathable droplets, which form an aerosolized (atomized) mist. In some embodiments, when the patient breathes in, a valve at the top opens, which then allows air into the apparatus, thereby speeding up the mist generation; when the patient breathes out, the top valve closes, thereby slowing down the mist generation while simultaneously permitting the patient to breathe out through the opening of a mouthpiece flap. Some nebulizers may provide the aerosol in a continuous mode (e.g., the eFlow from PARI Pharma Starnberg), by a breath enhanced mode (e.g., the PARI LC Plus or Sprint from PARI Starnberg), by breath actuated mode dependent on the breathing pattern of the patient (e.g., the AeroEclipse from Trudell, Canada or the I-Neb from Philips Respironics), or according to given inhalation profile (e.g., the Akita from Activaero, Gmuenden, Germany).

Some conventional inhalation devices are disclosed in U.S. Pat. Nos. 6,513,727, 6,513,519, 6,176,237, 6,085,741, 6,000,394, 5,957,389, 5,740,966, 5,549,102, 5,461,695, 5,458,136, 5,312,046, 5,309,900, 5,280,784, and 4,496,086, each of which is hereby incorporated by reference in its entirety. Commercial conventional inhalation devices are available from: PARI (Germany) under the trade names PARI LC Plus®, LC Star®, and PARI-Jet®; A & H Products, Inc. (Tulsa, Okla.) under the trade name AquaTower®; Hudson RCI (Temecula, Calif.) under the trade name AVA-NEB®; Intersurgical, Inc. (Liverpool, N.Y.) under the trade name Cirrus®; Salter Labs (Arvin, Calif.) under the trade name Salter 8900®; Respironics (Murrysville, Pa.) under the trade name Sidestream®; Bunnell (Salt Lake City, Utah) under the trade name Whisper Jet®; Smiths-Medical (Hyth Kent, UK) under the trade name Downdraft®, and DeVilbiss (Somerset, Pa.) under the trade name DeVilbiss®; or Trudell, Canada under the trade name AeroEclipse®.

In some embodiments of the methods disclosed herein, compositions comprising mast cell stabilizers are administered with a dry powder inhaler. In some embodiments of the methods disclosed herein, compositions administered with dry powder inhalers comprise one or more of nanoparticles, spray dried materials, engineered porous particles with low mass median diameter but a high geometric diameter, liposomes, and stealth (or PEGylated) liposomes. In some embodiments, compositions administered by dry powder inhalers administered in the methods disclosed herein comprise nanoparticle clusters that aggregate into micrometer sized particles at neutral or basic pH but dissociate into nanoparticles at the pH encountered in the lung. In some embodiments the nanoparticle clusters comprise fumaryl diketopiperazine. In some embodiments, compositions administered with dry powder inhalers comprise lactose. In some embodiments, compositions administered with dry powder inhalers do not comprise lactose. In some embodiments, compositions administered with a dry powder inhaler have a MMAD between 2 and 4 µm, a GSD between 1.5 and 2.5 µm, and an RF (≤5 µm) between 30% and 80%. In some embodiments, a dry powder inhaler used to administer an inhalation formulation in the methods disclosed herein comprises a pre-metered dose, such as Plastiape Monodose inhaler, which comprises a capsule pre-filled with a powder. In some embodiments, a dry powder inhaler used to administer an inhalation formulation in the methods disclosed herein has a device-metered system such as Twisthaler, sold by Schering Plough, which comprises a reservoir to store a powder and a twisting top to dispense each dose. Inhalation formulations for administration with a dry powder inhaler may be prepared by blending a mast cell stabilizer, e.g., cromolyn sodium, with lactose, or spray drying a mast cell stabilizer, e.g., cromolyn sodium, or by pelletizing a mast cell stabilizer, e.g., cromolyn sodium, to form free-flowing spherical agglomerates.

In some embodiments of the methods disclosed herein, compositions comprising mast cell stabilizers are administered with a metered dose inhaler. In some embodiments, a composition administered with a metered dose inhaler in the methods disclosed herein comprises one or more of nanoparticles, spray dried materials, engineered porous particles with low mass median diameter but a high geometric diameter, liposomes, and stealth (or PEGylated) liposomes.

In some embodiments of the methods disclosed herein, compositions comprising mast cell stabilizers are administered with a thermal aerosol inhaler. In some embodiments, the aerosol in a thermal aerosol inhaler is generated by directly heating and vaporizing a thin solid film of the mast cell stabilizer, e.g., cromolyn sodium, or by heating and vaporizing a solution of a mast cell stabilizer, e.g., cromolyn sodium in solvents such as propylene glycol and/or glycerol and water.

In some embodiments of the methods disclosed herein, compositions comprising mast cell stabilizers are administered with an electrohydrodynamic-based solution misting inhaler. In some embodiments, the aerosol in the electrohydrodynamic-based solution-misting inhaler is generated by subjecting a solution of a mast cell stabilizer, e.g., cromolyn sodium, or a liposome or pegylated liposome comprising a mast cell stabilizer, e.g., cromolyn sodium, to electrohydrodynamic forces through electrostatic energy.

High Efficiency Nebulizers

High efficiency nebulizers are inhalation devices that comprise a micro-perforated membrane through which a liquid solution is converted through electrical or mechanical means into aerosol droplets suitable for inhalation. High efficiency nebulizers can deliver a large fraction of a loaded dose to a patient. In some embodiments, the high efficiency nebulizer also utilizes one or more actively or passively vibrating microperforated membranes. In some embodiments, the high efficiency nebulizer contains one or more oscillating membranes. In some embodiments, the high efficiency nebulizer contains a vibrating mesh or plate with multiple apertures and optionally a vibration generator with an aerosol mixing chamber. In some such embodiments, the mixing chamber functions to collect (or stage) the aerosol from the aerosol generator. In some embodiments, an inhalation valve is also used to allow an inflow of ambient air into the mixing chamber during an inhalation phase and is closed to prevent escape of the aerosol from the mixing chamber during an exhalation phase. In some such embodiments, the exhalation valve is arranged at a mouthpiece which is removably mounted at the mixing chamber and through which the patient inhales the aerosol from the mixing chamber. Still yet, in some embodiments, the high efficiency nebulizer contains a pulsating membrane. In some embodiments, the high efficiency nebulizer is continuously operating.

In some embodiments, the high efficiency nebulizer contains a vibrating micro-perforated membrane of tapered nozzles that generates a plume of droplets without the need for compressed gas. In these embodiments, a solution in the micro-perforated membrane nebulizer is in contact with a membrane, the opposite side of which is open to the air. The membrane is perforated by a large number of nozzle orifices of an atomizing head. An aerosol is created when alternating acoustic pressure in the solution is built up in the vicinity of the membrane causing the fluid on the liquid side of the membrane to be emitted through the nozzles as uniformly sized droplets.

Some embodiments of high efficiency nebulizers use passive nozzle membranes and a separate piezoelectric transducer that stimulates the membrane. In contrast, some high efficiency nebulizers employ an active nozzle membrane, which use the acoustic pressure in the nebulizer to generate very fine droplets of solution via the high frequency vibration of the nozzle membrane.

Some high efficiency nebulizers contain a resonant system. In some such high efficiency nebulizers, the membrane is driven by a frequency for which the amplitude of the vibrational movement at the center of the membrane is particularly large, resulting in a focused acoustic pressure in the vicinity of the nozzle; the resonant frequency may be about 100 kHz. A flexible mounting is used to keep unwanted loss of vibrational energy to the mechanical surroundings of the atomizing head to a minimum. In some embodiments, the vibrating membrane of the high efficiency nebulizer may be made stainless steel, or of a nickel-palladium alloy by electroforming.

In some embodiments, a high efficiency nebulizer may be adapted or adaptable to operate in conjunction with a unit dosage form, such as an ampule or vial, which contains a single dose of a mast cell stabilizer composition for the treatment of a lung disease or condition. The unit dosage form comprises a container that contains an inhalation formulation comprising the mast cell stabilizer, such as cromolyn sodium. The container is adapted to cooperate with the high efficiency nebulizer device in such a way as to permit administration of the nominal dose of the inhalation formulation to a patient. In some embodiments, the high efficiency nebulizer and the unit dosage form are configured so that they are useable together, but not with other devices or dosage forms. In some particular embodiments, the unit dosage form is configured such that it fits into a keyhole-like structure in the high efficiency nebulizer, but will not operate with other nebulizer devices. In such embodiments, the high efficiency nebulizer is configured such that it will accept and properly operate with the unit dosage form containing the mast cell stabilizer, but not with other dosage forms.

Commercial high efficiency nebulizers are available from: PARI (Germany) under the trade name eFlow®; Aerogen, Ltd. (Ireland) under the trade names AeroNeb® Go and AeroNeb® Pro, AeroNeb® Solo, and other nebulizers utilizing the OnQ® nebulizer technology; Respironics (Murrysville, Calif.) under the trade names I-Neb®; Omron (Bannockburn, Ill.) under the trade name Micro-Air®; Activaero (Germany) under the trade name Akita®, and AerovectRx (Atlanta, Ga.) under the trade name AerovectRx®.

In some embodiments, the DD expressed as the percentage of the nominal dose of a mast cell stabilizer administered with a high efficiency nebulizer in the methods disclosed herein is at least about 30%, at least about 35%, at least about 40%, at least about 45%, at least about 50%, at least about 55%, at least about 60%, at least about 65%, about 65%, about 70%, about 30% to about 90%, about 40% to about 80%, about 45% to about 75%, about 50% to about 70%, about 30% to about 75%, about 40% to about 70%, about 45% to about 60%, or about 60% to about 70%.

TOR is the speed at which the liquid containing a mast cell stabilizer is administered from the inhalation device. In some embodiments, administration of the mast cell stabilizer with the high efficiency nebulizer provides a TOR of at least about 2 times, 3 times or 4 times the TOR achievable with a conventional inhalation device, such as a nebulizer. For example, in some embodiments the TOR is at least about at least about 150 mg/min, at least about 200 mg/min, at least about 250 mg/min, at least 300 mg/min, at least 350 mg/min, at least 400 mg/min, at least 500 mg/min, or from 200 to about 700 mg/min.

In some embodiments, use of a high efficiency nebulizer in the methods disclosed herein provides a RF (≤3.3 μm) of mast cell stabilizer of at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, about 20% to about 95%, about 35% to about 90%, or about 40% to about 80%, about 40% to about 90%, about 40% to about 95%, about 45% to about 90%, about 45% to about 95%, about 50% to about 90%, about 65% to about 90%, about 60% to about 95%, about 65% to about 95%, about 70% to about 90%, or about 55% to about 90%. In some embodiments, use of a high efficiency nebulizer in the methods disclosed herein provides a RF (≤3.3 μm) of cromolyn sodium of at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, about 20% to about 95%, about 35% to about 90%, or about 40% to about 80%, about 40% to about 90%, about 40% to about 95%, about 45% to about 90%, about 45% to about 95%, about 50% to about 90%, about 65% to about 90%, about 60% to about 95%, about 65% to about 95%, about 70% to about 90%, about 55% to about 90%, about 40% to about 50%, about 35% to about 45%, about 35% to about 50%, about 30% to about 50%, about 44%, or about 36%.

In some embodiments, use of a high efficiency nebulizer in the methods disclosed herein provides a RF (1-5 μm) of mast cell stabilizer of at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, about 20% to about 95%, about 35% to about 90%, or about 40% to about 80%, about 40% to about 90%, about 40% to about 95%, about 45% to about 90%, about 45% to about 95%, about 50% to about 90%, about 65% to about 90%, about 60% to about 95%, about 65% to about 95%, about 70% to about 90%, or about 55% to about 90%. In some embodiments, use of a high efficiency nebulizer in the methods disclosed herein provides a RF (1-5 μm) of cromolyn sodium of at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, about 20% to about 95%, about 35% to about 90%, or about 40% to about 80%, about 40% to about 90%, about 40% to about 95%, about 45% to about 90%, about 45% to about 95%, about 50% to about 90%, about 65% to about 90%, about 60% to about 95%, about 65% to about 95%, about 70% to about 90%, or about 55% to about 90%.

In some embodiments, use of a high efficiency nebulizer in the methods disclosed herein provides a RF (≤5 μm) of mast cell stabilizer of at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, about 20% to about 95%, about 35% to about 90%, or about 40% to about 80%, about 40% to about 90%, about 40% to about 95%, about 45% to about 90%, about 45% to about 95%, about 50% to about 90%, about 65% to about 90%, about 60% to about 95%, about 65% to about 95%, about 70% to about 90%, or about 55% to about 90%. In some embodiments, use of a high efficiency nebulizer in the methods disclosed herein provides a RF (≤5 μm) of cromolyn sodium of at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, about 20% to about 95%, about 35% to about 90%, or about 40% to about 80%, about 40% to about 90%, about 40% to about 95%, about 45% to about 90%, about 45% to about 95%, about 50% to about 90%, about 65% to about 90%, about 60% to about 95%, about 65% to about 95%, about 70% to about 90%, about 55% to about 90%, about 70% to about 80%, about 65% to about 75%, about 65% to about 80%, about 60% to about 80%, about 66%, or about 75%.

In some embodiments, use of a high efficiency nebulizer in the methods disclosed herein provides a RDDR of at least about 2 times, at least about 3 times or at least about 4 times the RDDR achievable with a conventional inhalation device. For example, where the mast cell stabilizer is cromolyn sodium, in some embodiments the RDDR is at least about 5 mg/min, at least about 10 mg/min, at least about 15 mg/min, at least about 20 mg/min, at least about 25 mg/min, at least about 30 mg/min, at least about 35 mg/min, at least about 40 mg/min, at least about 45 mg/min, at least about 50 mg/min, at least about 55 mg/min, or at least about 60 mg/min.

In some embodiments, administration of a mast cell stabilizer with a high efficiency nebulizer in the methods disclosed herein provides a GSD of emitted droplet size distribution of about 1.1 to about 2.1, about 1.2 to about 2.0, about 1.3 to about 1.9, less than about 2, at least about 1.4 to about 1.8, at least about 1.5 to about 1.7, about 1.4, about 1.5, about 1.6, or about 1.7. In some embodiments, administration of a mast cell stabilizer with a high efficiency nebulizer in the methods disclosed herein provides a MMAD of droplet size of about 1 µm to about 5 µm, about 2 to about 4 µm, about 3 to about 4 µm, about 3.5 to about 4.5 µm, or about 3.5 µm. In some particular embodiments, administration of a mast cell stabilizer in the methods disclosed herein provides droplets having a particular combination of MMAD and GSD, for example: an MMAD of less than about 5 µm and a GSD of about 1.1 to about 2.1; an MMAD of less than about 4.5 µm and a GSD of about 1.1 to about 2.1; an MMAD of about 1 µm to about 5 µm and a GSD of about 1.1 to about 2.1; an MMAD of about 1.5 to about 4.5 µm and a GSD of about 1.1 to about 2.1; an MMAD of less than about 5 µm and a GSD of about 1.1 to about 2.0; an MMAD of less than about 4.5 µm and a GSD of about 1.1 to about 2.0; an MMAD of about 1 µm to about 5 µm and a GSD of about 1.1 to about 2.0; an MMAD of about 1.5 to about 4.5 µm and a GSD of about 1.1 to about 2.0; an MMAD of less than about 5 µm and a GSD of about 1.1 to about 1.9; an MMAD of less than about 4.5 µm and a GSD of about 1.1 to about 1.9; an MMAD of about 1 µm to about 5 µm and a GSD of about 1.1 to about 1.9; an MMAD of about 1.5 to about 4.5 µm and a GSD of about 1.1 to about 1.9; an MMAD of less than about 5 µm and a GSD of about 1.1 to about 1.8; an MMAD of less than about 4.5 µm and a GSD of about 1.1 to about 1.8; an MMAD of about 1 µm to about 5 µm and a GSD of about 1.1 to about 1.8; an MMAD of about 1.5 to about 4.5 µm and a GSD of about 1.1 to about 1.8; an MMAD of about 3.5 µm or less and a GSD of about 1.7; an MMAD of about 4.1 µm or less and a GSD of about 1.7; an MMAD of about 3.5 µm and a GSD of about 1.7; or an MMAD of about 4.1 µm and a GSD of about 1.7.

In some embodiments, the median particle size of a mast cell stabilizer aerosol administered with a high efficiency nebulizer is between about 1 µm and about 6 µm, between about 2 µm and about 5 µm, between about 3 µm and about 5 µm, between about 3 µm and about 4 µm, about 1 µm, about 2 µm, about 3 µm, about 4 µm, about 5 µm, or about 6 µm. In some embodiments, the median particle size of cromolyn sodium aerosol administered with a high efficiency nebulizer is between about 1 µm and about 6 µm, between about 2 µm and about 5 µm, between about 3 µm and about 5 µm, between about 3 µm and about 4 µm, about 1 µm, about 2 µm, about 3 µm, about 4 µm, about 5 µm, or about 6 µm.

Inhalation Formulations

In some embodiments of the methods disclosed herein, inhalation formulations are administered with an inhalation device to provide a systemically effective amount of a mast cell stabilizer and a locally effective amount of the mast cell stabilizer for the treatment of a lung disease or condition. In some embodiments of the methods disclosed herein, inhalation formulations are administered with an inhalation device to provide a systemically effective amount of a mast cell stabilizer and a high deposited lung dose of the mast cell stabilizer for the treatment of a lung disease or condition. In some embodiments of the methods disclosed herein, inhalation formulations are administered with an inhalation device to provide a systemically effective amount of a mast cell stabilizer, a locally effective amount of a mast cell stabilizer, and a high deposited lung dose of the mast cell stabilizer for the treatment of a lung disease or condition. In some embodiments, the methods disclosed herein comprise administering a nominal dose of one or more mast cell stabilizers in an aqueous inhalation solution to the patient with an inhalation device, e.g., a high efficiency nebulizer.

In some embodiments of the methods disclosed herein, an inhalation formulation administered with an inhalation device, e.g., a high efficiency nebulizer, produces in a human subject group an average $AUC_{(0-\infty)}$ of a mast cell stabilizer greater than about 100 ng*hr/mL, greater than about 110 ng*hr/mL, greater than about 120 ng*hr/mL, greater than about 130 ng*hr/mL, greater than about 140 ng*hr/mL, greater than about 150 ng*hr/mL, greater than about 160 ng*hr/mL, greater than about 170 ng*hr/mL, greater than about 180 ng*hr/mL, greater than about 190 ng*hr/mL, greater than about 200 ng*hr/mL, greater than about 225 ng*hr/mL, greater than about 250 ng*hr/mL, greater than about 275 ng*hr/mL, greater than about 300 ng*hr/mL, greater than about 325 ng*hr/mL, greater than about 350 ng*hr/mL, greater than about 375 ng*hr/mL, greater than about 400 ng*hr/mL, greater than about 425 ng*hr/mL, greater than about 450 ng*hr/mL, greater than about 475 ng*hr/mL, greater than about 500 ng*hr/mL, greater than about 525 ng*hr/mL, greater than about 550 ng*hr/mL, greater than about 575 ng*hr/mL, greater than about 600 ng*hr/mL, greater than about 625 ng*hr/mL, greater than about 650 ng*hr/mL, greater than about 675 ng*hr/mL, greater than about 700 ng*hr/mL, greater than about 725 ng*hr/mL, greater than about 750 ng*hr/mL, greater than about 775 ng*hr/mL, greater than about 800 ng*hr/mL, greater than about 825 ng*hr/mL, greater than about 850 ng*hr/mL, greater than about 875 ng*hr/mL, greater than about 900 ng*hr/mL, greater than about 925 ng*hr/mL, greater than about 950 ng*hr/mL, greater than about 975 ng*hr/mL, or greater than about 1000 ng*hr/mL after administration of the formulation to the patient. In some embodiments of the methods disclosed herein, an inhalation formulation administered with an inhalation device, e.g., a high efficiency nebulizer, produces in a human subject group an average $AUC_{(0-\infty)}$ of a mast cell stabilizer of about 100 ng*hr/mL, about 110 ng*hr/mL, about 120 ng*hr/mL, about 130 ng*hr/mL, about 140 ng*hr/mL, about 150 ng*hr/mL, about 160 ng*hr/mL, about 170 ng*hr/mL, about 180 ng*hr/mL, about 190 ng*hr/mL, about 200 ng*hr/mL, about 225 ng*hr/mL, about 250 ng*hr/mL, about 275 ng*hr/mL, about 300 ng*hr/mL, about 325 ng*hr/mL, about 350 ng*hr/mL, about 375 ng*hr/mL, about 400 ng*hr/mL, about 425 ng*hr/mL, about 450 ng*hr/mL, about 475 ng*hr/mL, about 500 ng*hr/mL, about 525 ng*hr/mL, about 550 ng*hr/mL, about 575 ng*hr/mL, about 600 ng*hr/mL, about 625 ng*hr/mL, about 650 ng*hr/mL, about 675 ng*hr/mL, about 700 ng*hr/mL, about 725 ng*hr/mL, about 750 ng*hr/mL, about 775 ng*hr/mL, about 800 ng*hr/mL, about 825 ng*hr/mL, about 850 ng*hr/mL, about 875 ng*hr/mL, about 900 ng*hr/mL, about 925 ng*hr/mL, about 950 ng*hr/mL, about 975 ng*hr/mL, or about 1000 ng*hr/mL after administration of the formulation to the patient.

In some embodiments of the methods disclosed herein, an inhalation formulation administered with an inhalation device, e.g., a high efficiency nebulizer, produces in a human subject group an average $AUC_{(0-\infty)}$ of cromolyn sodium greater than about 100 ng*hr/mL, greater than about 110 ng*hr/mL, greater than about 120 ng*hr/mL, greater than about 130 ng*hr/mL, greater than about 140 ng*hr/mL, greater than about 150 ng*hr/mL, greater than about 160 ng*hr/mL, greater than about 170 ng*hr/mL, greater than about 180 ng*hr/mL, greater than about 190 ng*hr/mL, greater than about 200 ng*hr/mL, greater than about 225 ng*hr/mL, greater than about 250 ng*hr/mL, greater than about 275 ng*hr/mL, greater than about 300 ng*hr/mL, greater than about 325 ng*hr/mL, greater than about 350 ng*hr/mL, greater than about 375 ng*hr/mL, greater than about 400 ng*hr/mL, greater than about 425 ng*hr/mL, greater than about 450 ng*hr/mL, greater than about 475 ng*hr/mL, greater than about 500 ng*hr/mL, greater than about 525 ng*hr/mL, greater than about 550 ng*hr/mL, greater than about 575 ng*hr/mL, greater than about 600 ng*hr/mL, greater than about 625 ng*hr/mL, greater than about 650 ng*hr/mL, greater than about 675 ng*hr/mL, greater than about 700 ng*hr/mL, greater than about 725 ng*hr/mL, greater than about 750 ng*hr/mL, greater than about 775 ng*hr/mL, greater than about 800 ng*hr/mL, greater than about 825 ng*hr/mL, greater than about 850 ng*hr/mL, greater than about 875 ng*hr/mL, greater than about 900 ng*hr/mL, greater than about 925 ng*hr/mL, greater than about 950 ng*hr/mL, greater than about 975 ng*hr/mL, or greater than about 1000 ng*hr/mL after administration of the formulation to the patient. In some embodiments of the methods disclosed herein, an inhalation formulation administered with an inhalation device, e.g., a high efficiency nebulizer, produces in a human subject group an average $AUC_{(0-\infty)}$ of cromolyn sodium of about 100 ng*hr/mL, about 110 ng*hr/mL, about 120 ng*hr/mL, about 130 ng*hr/mL, about 140 ng*hr/mL, about 150 ng*hr/mL, about 160 ng*hr/mL, about 170 ng*hr/mL, about 180 ng*hr/mL, about 190 ng*hr/mL, about 200 ng*hr/mL, about 225 ng*hr/mL, about 250 ng*hr/mL, about 275 ng*hr/mL, about 300 ng*hr/mL, about 325 ng*hr/mL, about 350 ng*hr/mL, about 375 ng*hr/mL, about 400 ng*hr/mL, about 425 ng*hr/mL, about 450 ng*hr/mL, about 475 ng*hr/mL, about 500 ng*hr/mL, about 525 ng*hr/mL, about 550 ng*hr/mL, about 575 ng*hr/mL, about 600 ng*hr/mL, about 625 ng*hr/mL, about 650 ng*hr/mL, about 675 ng*hr/mL, about 700 ng*hr/mL, about 725 ng*hr/mL, about 750 ng*hr/mL, about 775 ng*hr/mL, about 800 ng*hr/mL, about 825 ng*hr/mL, about 850 ng*hr/mL, about 875 ng*hr/mL, about 900 ng*hr/mL, about 925 ng*hr/mL, about 950 ng*hr/mL, about 975 ng*hr/mL, or about 1000 ng*hr/mL after administration of the formulation to the patient.

In some embodiments of the methods disclosed herein, an inhalation formulation administered with an inhalation device, e.g., a high efficiency nebulizer, produces in a human subject group an average $C_{max}$ of a mast cell stabilizer greater than about 40 ng/mL, greater than about 50 ng/mL, greater than about 60 ng/mL, greater than about 70 ng/mL, greater than about 80 ng/mL, greater than about 90 ng/mL, greater than about 100 ng/mL, greater than about 110 ng/mL, greater than about 120 ng/mL, greater than about 130 ng/mL, greater than about 140 ng/mL, greater than about 150 ng/mL, greater than about 160 ng/mL, greater than about 170 ng/mL, greater than about 180 ng/mL, greater than about 190 ng/mL, greater than about 200 ng/mL, greater than about 210 ng/mL, greater than about 220 ng/mL, greater than about 230 ng/mL, greater than about 240 ng/mL, greater than about 250 ng/mL, greater than about 260 ng/mL, greater than about 270 ng/mL, greater than about 280 ng/mL, greater than about 290 ng/mL, greater than about 300 ng/mL, greater than about 310 ng/mL, greater than about 320 ng/mL, greater than about 330 ng/mL, greater than about 340 ng/mL, greater than about 350 ng/mL, greater than about 360 ng/mL, greater than about 370 ng/mL, greater than about 380 ng/mL, greater than about 390 ng/mL, or greater than about 400 ng/mL after administration of the formulation to the patient. In some embodiments of the methods disclosed herein, an inhalation formulation administered with an inhalation device, e.g., a high efficiency nebulizer, produces in a human subject group an average $C_{max}$ of a mast cell stabilizer of about 50 ng/mL, about 60 ng/mL, about 70 ng/mL, about 80 ng/mL, 90 ng/mL, about 100 ng/mL, about 110 ng/mL, about 120 ng/mL, about 130 ng/mL, about 140 ng/mL, about 150 ng/mL, about 160 ng/mL, about 170 ng/mL, about 180 ng/mL, about 190 ng/mL, about 200 ng/mL, about 210 ng/mL, about 220 ng/mL, about 230 ng/mL, about 240 ng/mL, about 250 ng/mL, 260 ng/mL, about 270 ng/mL, about 280 ng/mL, about 290 ng/mL, about 300 ng/mL, about 310 ng/mL, about 320 ng/mL, about 330 ng/mL, about 340 ng/mL, about 350 ng/mL, about 360 ng/mL, about 370 ng/mL, about 380 ng/mL, about 390 ng/mL, or about 400 ng/mL after administration of the formulation to the patient.

In some embodiments of the methods disclosed herein, an inhalation formulation administered with an inhalation device, e.g., a high efficiency nebulizer, produces in a human subject group an average $C_{max}$ of cromolyn sodium greater than about 40 ng/mL, greater than about 50 ng/mL, greater than about 60 ng/mL, greater than about 70 ng/mL, greater than about 80 ng/mL, greater than about 90 ng/mL, greater than about 100 ng/mL, greater than about 110 ng/mL, greater than about 120 ng/mL, greater than about 130 ng/mL, greater than about 140 ng/mL, greater than about 150 ng/mL, greater than about 160 ng/mL, greater than about 170 ng/mL, greater than about 180 ng/mL, greater than about 190 ng/mL, greater than about 200 ng/mL, greater than about 210 ng/mL, greater than about 220 ng/mL, greater than about 230 ng/mL, greater than about 240 ng/mL, greater than about 250 ng/mL, greater than about 260 ng/mL, greater than about 270 ng/mL, greater than about 280 ng/mL, greater than about 290 ng/mL, greater than about 300 ng/mL, greater than about 310 ng/mL, greater than about 320 ng/mL, greater than about 330 ng/mL, greater than about 340 ng/mL, greater than about 350 ng/mL, greater than about 360 ng/mL, greater than about 370 ng/mL, greater than about 380 ng/mL, greater than about 390 ng/mL, or greater than about 400 ng/mL after administration of the formulation to the patient. In some embodiments of the methods disclosed herein, an inhalation formulation administered with an inhalation device, e.g., a high efficiency nebulizer, produces in a human subject group an average $C_{max}$ of cromolyn sodium of about 50 mg/mL, about 60 ng/mL, about 70 ng/mL, about 80 ng/mL, 90 ng/mL, about 100 ng/mL, about 110 ng/mL, about 120 ng/mL, about 130 ng/mL, about 140 ng/mL, about 150 ng/mL, about 160 ng/mL, about 170 ng/mL, about 180 ng/mL, about 190 ng/mL, about 200 ng/mL, about 210 ng/mL, about 220 ng/mL, about 230 ng/mL, about 240 ng/mL, about 250 ng/mL, 260 ng/mL, about 270 ng/mL, about 280 ng/mL, about 290 ng/mL, about 300 ng/mL, about 310 ng/mL, about 320 ng/mL, about 330 ng/mL, about 340 ng/mL, about 350 ng/mL, about 360 ng/mL, about 370 ng/mL, about 380 ng/mL, about 390 ng/mL, or about 400 ng/mL after administration of the formulation to the patient.

In some embodiments of the methods disclosed herein, an inhalation formulation administered with an inhalation device, e.g., a high efficiency nebulizer, produces in a human subject group an average $AUC_{(0-\infty)}$ of a mast cell stabilizer greater than about 120 ng*hr/mL and/or an average $C_{max}$ of the mast cell stabilizer greater than about 55 ng/mL. In some embodiments of the methods disclosed herein, an inhalation formulation administered with an inhalation device, e.g., a high efficiency nebulizer, produces in a human subject group an average $AUC_{(0-\infty)}$ of a mast cell stabilizer greater than about 120 ng*hr/mL and an average $C_{max}$ of the mast cell stabilizer greater than about 55 ng/mL. In some embodiments of the methods disclosed herein, an inhalation formulation administered with an inhalation device, e.g., a high efficiency nebulizer, produces in a human subject group an average $AUC_{(0-\infty)}$ of a mast cell stabilizer greater than about 200 ng*hr/mL and an average $C_{max}$ of the mast cell stabilizer greater than about 80 ng/mL. In some embodiments of the methods disclosed herein, an inhalation formulation administered with an inhalation device, e.g., a high efficiency nebulizer, produces in a human subject group an average $AUC_{(0-\infty)}$ of a mast cell stabilizer greater than about 330 ng*hr/mL and an average $C_{max}$ of the mast cell stabilizer greater than about 150 ng/mL. In some embodiments, of the methods disclosed herein, an inhalation formulation administered with an inhalation device, e.g., a high efficiency nebulizer, produces in a human subject group an average $AUC_{(0-\infty)}$ of a mast cell stabilizer greater than about 525 ng*hr/mL and an average $C_{max}$ of the mast cell stabilizer greater than about 230 ng/mL.

In some embodiments of the methods disclosed herein, an inhalation formulation administered with an inhalation device, e.g., a high efficiency nebulizer, produces in a human subject group an average $AUC_{(0-\infty)}$ of cromolyn sodium greater than about 120 ng*hr/mL and/or an average $C_{max}$ of cromolyn sodium greater than about 55 ng/mL. In some embodiments of the methods disclosed herein, an inhalation formulation administered with an inhalation device, e.g., a high efficiency nebulizer, produces in a human subject group an average $AUC_{(0-\infty)}$ of cromolyn sodium greater than about 120 ng*hr/mL and an average $C_{max}$ of cromolyn sodium greater than about 55 ng/mL. In some embodiments of the methods disclosed herein, an inhalation formulation administered with an inhalation device, e.g., a high efficiency nebulizer, produces in a human subject group an average $AUC_{(0-\infty)}$ of cromolyn sodium greater than about 200 ng*hr/mL and an average $C_{max}$ of cromolyn sodium greater than about 80 ng/mL. In some embodiments of the methods disclosed herein, an inhalation formulation administered with an inhalation device, e.g., a high efficiency nebulizer, produces in a human subject group an average $AUC_{(0-\infty)}$ of cromolyn sodium greater than about 330 ng*hr/mL and an average $C_{max}$ of cromolyn sodium greater than about 150 ng/mL. In some embodiments, of the methods disclosed herein, an inhalation formulation administered with an inhalation device, e.g., a high efficiency nebulizer, produces in a human subject group an average $AUC_{(0-\infty)}$ of cromolyn sodium greater than about 525 ng*hr/mL and an average $C_{max}$ of cromolyn sodium greater than about 230 ng/mL.

In some embodiments of the methods disclosed herein, an inhalation formulation administered with an inhalation device, e.g., a high efficiency nebulizer, produces in a human subject group an average $AUC_{(0-\infty)}$ of cromolyn sodium of about 200 ng*hr/mL and an average $C_{max}$ of cromolyn sodium of about 80 ng/mL when a nominal dose of 40 mg of cromolyn sodium is administered with the inhalation device. In some embodiments of the methods disclosed herein, an inhalation formulation administered with an inhalation device, e.g., a high efficiency nebulizer, produces in a human subject group an average $AUC_{(0-\infty)}$ of cromolyn sodium of about 330 ng*hr/mL and an average $C_{max}$ of cromolyn sodium of about 150 ng/mL when a nominal dose of 40 mg of cromolyn sodium is administered with the inhalation device. In some embodiments of the methods disclosed herein, an inhalation formulation administered with an inhalation device, e.g., a high efficiency nebulizer, produces in a human subject group an average $AUC_{(0-\infty)}$ of cromolyn sodium of about 525 ng*hr/mL and an average $C_{max}$ of cromolyn sodium of about 230 ng/mL when a nominal dose of 80 mg of cromolyn sodium is administered with the inhalation device.

In some embodiments of the methods disclosed herein, an inhalation formulation administered with an inhalation device, e.g., a high efficiency nebulizer, produces in a human subject group an average $AUC_{(0-\infty)}$ of cromolyn sodium of about 180 ng*hr/mL to about 220 ng*hr/mL and an average $C_{max}$ of cromolyn sodium of about 70 ng/mL to about 90 ng/mL when a nominal dose of 40 mg of cromolyn sodium is administered with the inhalation device. In some embodiments of the methods disclosed herein, an inhalation formulation administered with an inhalation device, e.g., a high efficiency nebulizer, produces in a human subject group an average $AUC_{(0-\infty)}$ of cromolyn sodium of about 300 ng*hr/mL to about 360 ng*hr/mL and an average $C_{max}$ of cromolyn sodium of about 135 ng/mL to about 165 ng/mL when a nominal dose of 40 mg of cromolyn sodium is administered with the inhalation device. In some embodiments, of the methods disclosed herein, an inhalation formulation administered with an inhalation device, e.g., a high efficiency nebulizer, produces in a human subject group an average $AUC_{(0-\infty)}$ of cromolyn sodium of about 475 ng*hr/mL to about 575 ng*hr/mL and an average $C_{max}$ of cromolyn sodium of about 200 ng/mL to about 260 ng/mL when a nominal dose of 80 mg of cromolyn sodium is administered with the inhalation device.

In some embodiments of the methods disclosed herein, an inhalation formulation administered with an inhalation device, e.g., a high efficiency nebulizer, produces in a human subject group an average $AUC_{(0-\infty)}$ of a mast cell stabilizer greater than about 120 ng*hr/mL and a deposited lung dose of the mast cell stabilizer greater than about 30%. In some embodiments of the methods disclosed herein, an inhalation formulation administered with an inhalation device, e.g., a high efficiency nebulizer, produces in a human subject group an average $AUC_{(0-\infty)}$ of a mast cell stabilizer greater than about 200 ng*hr/mL and a deposited lung dose of the mast cell stabilizer greater than about 30%. In some embodiments of the methods disclosed herein, an inhalation formulation administered with an inhalation device, e.g., a high efficiency nebulizer, produces in a human subject group an average $AUC_{(0-\infty)}$ of a mast cell stabilizer greater than about 330 ng*hr/mL and a deposited lung dose of the mast cell stabilizer greater than about 30%. In some embodiments of the methods disclosed herein, an inhalation formulation administered with an inhalation device, e.g., a high efficiency nebulizer, produces in a human subject group an average $AUC_{(0-\infty)}$ of a mast cell stabilizer greater than about 525 ng*hr/mL.

In some embodiments of the methods disclosed herein, an inhalation formulation administered with an inhalation device, e.g., a high efficiency nebulizer, produces in a human subject group an average $AUC_{(0-\infty)}$ of cromolyn sodium greater than about 120 ng*hr/mL and a deposited lung dose of cromolyn sodium greater than about 30%. In some embodiments of the methods disclosed herein, an inhalation formulation administered with an inhalation device, e.g., a high efficiency nebulizer, produces in a human subject group an average $AUC_{(0-\infty)}$ of cromolyn sodium greater than about 200 ng*hr/mL and a deposited lung dose of cromolyn sodium greater than about 30%. In some embodiments of the methods disclosed herein, an inhalation formulation administered with an inhalation device, e.g., a high efficiency nebulizer, produces in a human subject group an average $AUC_{(0-\infty)}$ of cromolyn sodium greater than about 330 ng*hr/mL and a deposited lung dose of cromolyn sodium greater than about 30%. In some embodiments, of the methods disclosed herein, an inhalation formulation administered with an inhalation device, e.g., a high efficiency nebulizer, produces in a human subject group an average $AUC_{(0-\infty)}$ of cromolyn sodium greater than about 525 ng*hr/mL and a deposited lung dose of cromolyn sodium greater than about 30%.

In some embodiments of the methods disclosed herein, an inhalation formulation comprising 40 mg cromolyn sodium administered with an inhalation device, e.g., a high efficiency nebulizer, produces in a human subject group an average $AUC_{(0-\infty)}$ of cromolyn sodium greater than about 200 ng*hr/mL and a deposited lung dose of cromolyn sodium greater than about 30%. In some embodiments of the methods disclosed herein, an inhalation formulation comprising 40 mg cromolyn sodium administered with an inhalation device, e.g., a high efficiency nebulizer, produces in a human subject group an average $AUC_{(0-\infty)}$ of cromolyn sodium greater than about 330 ng*hr/mL and a deposited lung dose of cromolyn sodium greater than about 30%. In some embodiments, of the methods disclosed herein, an inhalation formulation comprising 80 mg cromolyn sodium administered with an inhalation device, e.g., a high efficiency nebulizer, produces in a human subject group an average $AUC_{(0-\infty)}$ of cromolyn sodium greater than about 525 ng*hr/mL and a deposited lung dose of cromolyn sodium greater than about 30%.

In some embodiments of the methods disclosed herein, an inhalation formulation administered with an inhalation device, e.g., a high efficiency nebulizer, has an RF (≤3.3 µm) of at least about 30% and produces in a human subject group an average $AUC_{(0-\infty)}$ of a mast cell stabilizer greater than about 120 ng*hr/mL. In some embodiments of the methods disclosed herein, an inhalation formulation administered with an inhalation device, e.g., a high efficiency nebulizer, has an RF (≤3.3 µm) of at least about 30% and produces in a human subject group an average $AUC_{(0-\infty)}$ of a mast cell stabilizer greater than about 200 ng*hr/mL. In some embodiments of the methods disclosed herein, an inhalation formulation administered with an inhalation device, e.g., a high efficiency nebulizer, has an RF (≤3.3 µm) of at least about 40% and produces in a human subject group an average $AUC_{(0-\infty)}$ of a mast cell stabilizer greater than about 330 ng*hr/mL. In some embodiments, of the methods disclosed herein, an inhalation formulation administered with an inhalation device, e.g., a high efficiency nebulizer, has an RF (≤3.3 µm) of at least about 40% and produces in a human subject group an average $AUC_{(0-\infty)}$ of a mast cell stabilizer greater than about 525 ng*hr/mL.

In some embodiments of the methods disclosed herein, an inhalation formulation administered with an inhalation device, e.g., a high efficiency nebulizer, has an RF (≤3.3 µm) of at least about 30% and produces in a human subject group an average $AUC_{(0-\infty)}$ of cromolyn sodium greater than about 120 ng*hr/mL. In some embodiments of the methods disclosed herein, an inhalation formulation administered with an inhalation device, e.g., a high efficiency nebulizer, has an RF (≤3.3 µm) of at least about 30% and produces in a human subject group an average $AUC_{(0-\infty)}$ of cromolyn sodium greater than about 200 ng*hr/mL. In some embodiments of the methods disclosed herein, an inhalation formulation administered with an inhalation device, e.g., a high efficiency nebulizer, has an RF (≤3.3 µm) of at least about 40% and produces in a human subject group an average $AUC_{(0-\infty)}$ of cromolyn sodium greater than about 330 ng*hr/mL. In some embodiments, of the methods disclosed herein, an inhalation formulation administered with an inhalation device, e.g., a high efficiency nebulizer, has an RF (≤3.3 µm) of at least about 40% and produces in a human subject group an average $AUC_{(0-\infty)}$ of cromolyn sodium greater than about 525 ng*hr/mL.

In some embodiments of the methods disclosed herein, an inhalation formulation comprising 40 mg cromolyn sodium administered with an inhalation device, e.g., a high efficiency nebulizer, has an RF (≤3.3 µm) of at least about 30% and produces in a human subject group an average $AUC_{(0-\infty)}$ of cromolyn sodium greater than about 200 ng*hr/mL. In some embodiments of the methods disclosed herein, an inhalation formulation comprising 40 mg cromolyn sodium administered with an inhalation device, e.g., a high efficiency nebulizer, has an RF (≤3.3 µm) of at least about 40% and produces in a human subject group an average $AUC_{(0-\infty)}$ of cromolyn sodium greater than about 330 ng*hr/mL. In some embodiments of the methods disclosed herein, an inhalation formulation comprising 80 mg cromolyn sodium administered with an inhalation device, e.g., a high efficiency nebulizer, has an RF (≤3.3 µm) of at least about 40% and produces in a human subject group an average $AUC_{(0-\infty)}$ of cromolyn sodium greater than about 525 ng*hr/mL.

In some embodiments of the methods disclosed herein, an inhalation formulation administered with an inhalation device, e.g., a high efficiency nebulizer, produces in a human subject group an average $AUC_{(0-\infty)}$ of cromolyn sodium of about 8.5 ng*hr/mL and an average $C_{max}$ of cromolyn sodium of about 3.9 ng/mL per mg of cromolyn sodium administered with the inhalation device. In some embodiments of the methods disclosed herein, an inhalation formulation administered with an inhalation device, e.g., a high efficiency nebulizer, produces in a human subject group an average $AUC_{(0-\infty)}$ of cromolyn sodium of about 6.6 ng*hr/mL and an average $C_{max}$ of cromolyn sodium of about 3.0 ng/mL per mg of cromolyn sodium administered with the inhalation device. In some embodiments of the methods disclosed herein, an inhalation formulation administered with an inhalation device, e.g., a high efficiency nebulizer, produces in a human subject group an average $AUC_{(0-\infty)}$ of cromolyn sodium of about 5.3 ng*hr/mL and an average $C_{max}$ of cromolyn sodium of about 2.2 ng/mL per mg of cromolyn sodium administered with the inhalation device. In some embodiments of the methods disclosed herein, an inhalation formulation administered with an inhalation device, e.g., a high efficiency nebulizer, produces in a human subject group an average $AUC_{(0-\infty)}$ of cromolyn sodium of from about 5.3 ng*hr/mL to about 8.5 ng*hr/mL and an average $C_{max}$ of cromolyn sodium of about 2.2 ng/mL to about 3.9 ng/mL per mg of cromolyn sodium administered with the inhalation device when the nominal dose of cromolyn sodium administered is in the range of about 40 mg to about 80 mg.

In some embodiments of the methods disclosed herein, an inhalation formulation administered with an inhalation device, e.g., a high efficiency nebulizer, provides mast cell stabilizer lung deposition (deposited lung dose) of at least about 15%, at least about 20%, at least about 25%, at least about 30%, at least about 35%, at least about 40%, at least about 45%, at least about 50%, at least about 55%, at least about 60%, about 20% to about 40%, about 25% to about 35%, about 25 to about 30%, about 25% to about 75%, about 30% to about 50%, about 35% to about 90%, about 40% to about 80%, about 40% to about 60%, about 50% to about 60%, about 50% to about 70%, or about 60% to about 75% based on the nominal dose of the mast cell stabilizer. In some embodiments of the methods disclosed herein, an inhalation formulation administered with an inhalation device, e.g., a high efficiency nebulizer, provides cromolyn sodium deposition (deposited lung dose) of at least about 15%, at least about 20%, at least about 25%, at least about 30%, at least about 35%, at least about 40%, at least about 45%, at least about 50%, at least about 55%, at least about 60%, about 20% to about 40%, about 25% to about 35%, about 25 to about 30%, about 25% to about 75%, about 30% to about 50%, about 35% to about 90%, about 40% to about 80%, about 40% to about 60%, about 50% to about 60%, about 50% to about 70%, or about 60% to about 75% based on the nominal dose of the cromolyn sodium.

In some embodiments of the methods disclosed herein, an inhalation formulation administered with an inhalation device, e.g., a high efficiency nebulizer, provides mast cell stabilizer lung deposition (deposited lung dose) of about 15%, about 20%, about 25%, about 30%, about 35%, about 40%, about 45%, about 50%, about 55%, about 60%, about 65%, about 70%, about 75% about 80%, about 85%, about 90%, about 95%, or about 100% based on the nominal dose of the mast cell stabilizer. In some embodiments of the methods disclosed herein, an inhalation formulation administered with an inhalation device, e.g., a high efficiency nebulizer, provides cromolyn sodium lung deposition (deposited lung dose) of about 15%, about 20%, about 25%, about 30%, about 35%, about 40%, about 45%, about 50%, about 55%, about 60%, about 65%, about 70%, about 75% about 80%, about 85%, about 90%, about 95%, or about 100% based on the nominal dose of the cromolyn sodium.

In some embodiments of the methods disclosed herein, an inhalation formulation administered with an inhalation device, e.g., a high efficiency nebulizer, provides mast cell stabilizer lung deposition (deposited lung dose) of greater than about 0.5 mg, greater than about 1 mg, greater than about 1.5 mg, greater than about 2 mg, greater than about 2.5 mg, greater than about 3 mg, greater than about 3.5 mg, greater than about 4 mg, greater than about 5 mg, greater than about 6 mg, greater than about 7 mg, greater than about 8 mg, greater than about 9 mg, greater than about 10 mg, greater than about 11 mg, greater than about 12 mg, greater than about 13 mg, greater than about 14 mg, or greater than about 15 mg. In some embodiments of the methods disclosed herein, an inhalation formulation administered with an inhalation device, e.g., a high efficiency nebulizer, provides mast cell stabilizer lung deposition (deposited lung dose) of about 0.5 mg, about 1.0 mg, about 1.5 mg, about 2.0 mg, about 2.5 mg, about 3.0 mg, about 3.5 mg, about 4.0 mg, about 5.0 mg, about 6.0 mg, about 7.0 mg, about 8.0 mg, about 9.0 mg, about 10 mg, about 11 mg, about 12 mg, about 13 mg, about 14 mg, or about 15 mg.

In some embodiments of the methods disclosed herein, an inhalation formulation administered with an inhalation device, e.g., a high efficiency nebulizer, provides cromolyn sodium lung deposition (deposited lung dose) of greater than about 0.5 mg, greater than about 1 mg, greater than about 1.5 mg, greater than about 2 mg, greater than about 2.5 mg, greater than about 3 mg, greater than about 3.5 mg, greater than about 4 mg, greater than about 5 mg, greater than about 6 mg, greater than about 7 mg, greater than about 8 mg, greater than about 9 mg, greater than about 10 mg, greater than about 11 mg, greater than about 12 mg, greater than about 13 mg, greater than about 14 mg, or greater than about 15 mg. In some embodiments of the methods disclosed herein, an inhalation formulation administered with an inhalation device, e.g., a high efficiency nebulizer, provides cromolyn sodium lung deposition (deposited lung dose) of about 0.5 mg, about 1.0 mg, about 1.5 mg, about 2.0 mg, about 2.5 mg, about 3.0 mg, about 3.5 mg, about 4.0 mg, about 5.0 mg, about 6.0 mg, about 7.0 mg, about 8.0 mg, about 9.0 mg, about 10 mg, about 11 mg, about 12 mg, about 13 mg, about 14 mg, or about 15 mg.

In some embodiments of the methods disclosed herein, an inhalation formulation containing a mast cell stabilizer is administered with an inhalation device, e.g., a high efficiency nebulizer, at an administration of less than about 1 mg/dose, about 1 mg/dose to about 100 mg/dose, about 5 mg/dose to about 80 mg/dose, about 20 mg/dose to about 60 mg/dose, about 30 mg/dose to about 50 mg/dose, or greater than 100 mg/dose. In some embodiments of the methods disclosed herein, an inhalation formulation containing cromolyn sodium is administered with an inhalation device, e.g., a high efficiency nebulizer, at an administration of less than about 1 mg/dose, about 1 mg/dose to about 100 mg/dose, about 5 mg/dose to about 80 mg/dose, about 20 mg/dose to about 60 mg/dose, about 30 mg/dose to about 50 mg/dose, or greater than 100 mg/dose. In some embodiments of the methods disclosed herein, a mast cell stabilizer is administered in an inhalation formulation with an inhalation device, e.g., a high efficiency nebulizer, in about 1 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg doses, about 135 mg, about 140 mg, about 145 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, or about 1000 mg doses. In some embodiments of the methods disclosed herein, cromolyn sodium is administered in an inhalation formulation with an inhalation device, e.g., a high efficiency nebulizer, in about 1 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg doses, about 135 mg, about 140 mg, about 145 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, or about 1000 mg doses.

In some embodiments of the methods disclosed herein, an inhalation formulation administered with an inhalation device, e.g., a high efficiency nebulizer provides a bioavailability of a mast cell stabilizer of greater than about 5%, greater than about 6%, greater than about 7%, greater than about 8%, greater than about 9%, greater than about 10%, greater than about 11%, greater than about 12%, greater than about 13%, greater than about 14%, greater than about 15%, greater than about 16%, greater than about 17%, greater than about 18%, greater than about 19%, greater than about 20%, greater than about 25%, greater than about 30%, greater than about 35%, greater than about 40%, greater than about 45%, greater than about 50%, greater than about 55%, or greater than about 60% of the nominal dose. In some embodiments, an inhalation formulation administered with an inhalation device, e.g., a high efficiency nebulizer, in the methods disclosed herein provides a bioavailability of a mast cell stabilizer of about 5%, about 6%, about 7%, about 8%, about 9%, about 10%, about 11%, about 12%, about 13%, about 14%, about 15%, about 16%, about 17%, about 18%, about 19%, about 20%, about 25%, about 30%, about 35%, about 40%, about 45%, about 50%, about 55%, or about 60% of the nominal dose.

In some embodiments of the methods disclosed herein, an inhalation formulation administered with an inhalation device, e.g., a high efficiency nebulizer provides a bioavailability of cromolyn sodium of greater than about 5%, greater than about 6%, greater than about 7%, greater than about 8%, greater than about 9%, greater than about 10%, greater than about 11%, greater than about 12%, greater than about 13%, greater than about 14%, greater than about 15%, greater than about 16%, greater than about 17%, greater than about 18%, greater than about 19%, greater than about 20%, greater than about 25%, greater than about 30%, greater than about 35%, greater than about 40%, greater than about 45%, or greater than about 50% of the nominal dose. In some embodiments, an aqueous inhalation formulation administered with an inhalation device, e.g., a high efficiency nebulizer, in the methods disclosed herein provides a bioavailability of cromolyn sodium of about 5%, about 6%, about 7%, about 8%, about 9%, about 10%, about 11%, about 12%, about 13%, about 14%, about 15%, about 16%, about 17%, about 18%, about 19%, about 20%, about 25%, about 30%, about 35%, about 40%, about 45%, or about 50% of the nominal dose.

In some embodiments of the methods disclosed herein, an inhalation formulation containing a mast cell stabilizer such as cromolyn sodium is administered with an inhalation device, e.g., a high efficiency nebulizer, at a fill volume of less than about 0.25 mL, less than about 0.5 mL, at least about 0.5 mL to about 1.5 mL, at least about 0.5 mL to about 1.8 mL, at least about 1.5 mL, or at least about 2.0 mL. In some embodiments, an inhalation formulation is administered with an inhalation device, e.g., a high efficiency nebulizer, at a fill volume about 0.1 mL to about 5.0 mL, about 0.25 mL to about 2.0 mL, about 0.5 mL to about 1.8 mL, about 0.5 mL to about 2 mL, about 0.5 mL to about 1.5 mL, about 0.5 mL to about 1.0 mL, about 0.5 mL or less, about 1 mL or less, about 1.5 mL or less, about 2.0 mL or less, about 2.5 mL or less, about 3.0 mL or less, about 3.5 mL or less, about 4.0 mL or less, about 4.5 mL or less, or about 5.0 mL or less. In some embodiments, an inhalation formulation is administered with an inhalation device, e.g., a high efficiency nebulizer, at a fill volume of about 0.5 mL, about 1.0 mL, about 1.5 mL, about 1.8 mL, about 2.0 mL, about 2.5 mL, about 3.0 mL, about 3.5 mL, about 4.0 mL, about 4.5 mL, or about 5.0 mL. In some embodiments, an inhalation formulation is administered with an inhalation device, e.g., a high efficiency nebulizer, which provides for a residual volume of mast cell stabilizer after administration of the mast cell stabilizer of less than about 10%, less than about 5%, or less than about 3% of the nominal dose.

In some embodiments of the methods disclosed herein, an inhalation formulation containing a mast cell stabilizer is administered with an inhalation device, e.g., a high efficiency nebulizer, wherein the concentration of the mast cell stabilizer is greater than about 1% by weight, greater than about 2% by weight, greater than about 3% by weight, greater than about 4% by weight, greater than about 5% by weight, greater than about 6% by weight, greater than about 7% by weight, greater than about 8% by weight, greater than about 9% by weight, or greater than about 10% by weight. In some embodiments of the methods disclosed herein, an inhalation formulation containing a mast cell stabilizer is administered with an inhalation device, e.g., a high efficiency nebulizer, wherein the concentration of the mast cell stabilizer is from about 1% by weight to about 10% by weight, from about 2% by weight to about 8% by weight, from about 2% by weight to about 6% by weight, or from about 3% by weight to about 5% by weight. In some embodiments of the methods disclosed herein, an inhalation formulation containing a mast cell stabilizer is administered with an inhalation device, e.g., a high efficiency nebulizer, wherein the concentration of the mast cell stabilizer is about 1% by weight, about 2% by weight, about 3% by weight, about 4% by weight, about 5% by weight, about 6% by weight, about 7% by weight, about 8% by weight, about 9% by weight, or about 10% by weight.

In some embodiments of the methods disclosed herein, an inhalation formulation containing cromolyn sodium is administered with an inhalation device, e.g., a high efficiency nebulizer, wherein the concentration of the cromolyn sodium is greater than about 1% by weight, greater than about 2% by weight, greater than about 3% by weight, greater than about 4% by weight, greater than about 5% by weight, greater than about 6% by weight, greater than about 7% by weight, greater than about 8% by weight, greater than about 9% by weight, or greater than about 10% by weight. In some embodiments of the methods disclosed herein, an inhalation formulation containing cromolyn sodium is administered with an inhalation device, e.g., a high efficiency nebulizer, wherein the concentration of the cromolyn sodium is from about 1% by weight to about 10% by weight, from about 2% by weight to about 8% by weight, from about 2% by weight to about 6% by weight, or from about 3% by weight to about 5% by weight. In some embodiments of the methods disclosed herein, an inhalation formulation containing cromolyn sodium is administered with an inhalation device, e.g., a high efficiency nebulizer, wherein the concentration of the cromolyn sodium is about 1% by weight, about 2% by weight, about 3% by weight, about 4% by weight, about 5% by weight, about 6% by weight, about 7% by weight, about 8% by weight, about 9% by weight, or about 10% by weight.

In some embodiments, an inhalation formulation containing a mast cell stabilizer is administered with an inhalation device, e.g., a high efficiency nebulizer, in about 0.25 to about 10 minutes, about 0.50 to about 8 minutes, less than about 8 minutes, less than about 7 minutes, less than about 6 minutes, less than about 5 minutes, less than about 4 minutes, less than about 3 minutes, less than about 2 minutes, less than about 1.8 minutes, less than about 1.5 minutes, or less than 1 minute. In some embodiments, the inhalation formulation is administered in about 3 minutes or less. In some embodiments, the inhalation formulation is administered in about 1 minute, about 2 minutes, about 3 minutes, about 4 minutes, about 5 minutes, about 6 minutes, about 7 minutes, about 8 minutes, about 9 minutes, or about 10 minutes.

In some embodiments of the methods disclosed herein, administration of a mast cell stabilizer with a high efficiency nebulizer provides at least about a 1.5-fold, at least about a 1.8-fold, at least about a two-fold, at least about a three-fold, at least about a four-fold, or at least about a five-fold increase in one or more of $AUC_{last}$, $AUC_{(0-\infty)}$, or $C_{max}$ as compared to the same or lower nominal dose of the mast cell stabilizer administered with a conventional inhalation device.

In some embodiments of the methods disclosed herein, inhalation formulations administered with a high efficiency nebulizer are substantially free of a preservative, such as benzyl alcohol. In some embodiments of the methods disclosed herein, inhalation formulations administered with a high efficiency nebulizer further comprise at least one excipient. In some embodiments, the excipient is selected from the group consisting of stabilizers and antioxidants (such as citric acid, ascorbic acid, ethylenediamine tetra acetic acid (EDTA), sodium metabisulfite, or a salt of any thereof), an osmolarity adjusting agent (such as sodium chloride, mannitol, or sorbitol), a surfactant (such as polysorbate 80, vitamin E, tocopherol polyethylene glycol, and Tyloxapol), or a pH buffer.

In some embodiments of the methods disclosed herein, inhalation formulations administered with an inhalation device, e.g., a high efficiency nebulizer, are hypotonic. In some embodiments of the methods disclosed herein, inhalation formulations administered with an inhalation device, e.g., a high efficiency nebulizer, are sub-isotonic. In some embodiments of the methods disclosed herein, inhalation formulations administered with an inhalation device, e.g., a high efficiency nebulizer, have an osmolality greater than about 70 mOsm/kg. In some embodiments of the methods disclosed herein, inhalation formulations administered with an inhalation device, e.g., high efficiency nebulizer, have an osmolality of at least about 100 mOsm/kg. In some embodiments of the methods disclosed herein, inhalation formulations administered with an inhalation device, e.g., high efficiency nebulizer, have an osmolality of at least about 150 mOsm/kg.

EXAMPLES

The examples below describe some embodiments of the methods described herein. Methods and materials that are not specifically described in the following examples are within the scope of the invention and will be apparent to those skilled in the art with reference to the disclosure herein.

Example 1: Formulations

The formulations described in Table 1 are prepared as follows: The composition ingredients are added sequentially to a glass beaker with a magnet stirrer and about 90 g of purified water in the order listed in Table 1, ensuring that each ingredient is dissolved before the next is added. The weight is then adjusted to 100.0 g by adding additional purified water. The resulting solutions are then sterilized by filtration through 0.2-0.22 μm sterile filters, and 0.5 to 5 mL aliquots are added to pre-sterilized glass or sterile polyethylene or polypropylene blow fill and seal vials by a standard blow fill and seal procedure. Alternative sterilization methods may be applied using heat sterilization in an autoclave.

Example 2: Characterization of an Aerosol Produced with a High Efficiency Nebulizer The MMAD, GSD, DD, and RF of a representative inhaled cromolyn sodium formulation (PA-101) delivered via a high efficiency nebulizer (eFlow®, PARI, 30 L) were determined as described in USP<1601>. The values determined were: MMAD=3.5 μm; GSD=1.7; DD=68%; RF (≤5 μm)=75%; and RF (≤3.3 μm)=44%.

The MMAD, GSD, and RF of a representative inhaled cromolyn sodium formulation (PA-101) delivered via a high efficiency nebulizer (eFlow®, PARI, 40 L) were determined as described in USP<1601>. The values determined were: MMAD=4.1 μm; GSD=1.7; RF (≤5 μm)=66%; and RF (≤3.3 μm)=36%.

Example 3: Single-Dose, Dose Escalation Study

Objectives

The objectives of the study are as follows:

Primary

To determine the systemic availability and pharmacokinetic (PK) profile of single doses of a representative inhaled cromolyn sodium formulation (PA-101) delivered via a high efficiency nebulizer (eFlow®, PARI) using two different aerosol membranes (30 L and 40 L) in comparison with marketed formulations of cromolyn sodium (oral solution and inhalation aerosol) in healthy subjects.

Secondary

To assess the safety and tolerability of PA-101 in comparison with marketed formulations of cromolyn sodium (oral solution and inhalation aerosol).

Methodology

This was a Phase 1, randomized, open-label, single-centre, dose-ranging, cross-over study conducted in a total of 12 healthy adult subjects of 18-45 years of age.

Study Treatments, Dose and Mode of Administration 1. 40 mg PA-101 (4% DSCG, 40 mg/1 mL), oral inhalation via eFlow 30 L.
2. 80 mg PA-101 (4% DSCG, 80 mg/2 mL), oral inhalation via eFlow 30 L.

TABLE 1

| | Formulation No. | | | | | | | | | | | | |
|---|---|---|---|---|---|---|---|---|---|---|---|---|---|
| | 1 | 2 | 3 | 4 | 5 | 6 | 7 | 8 | 9 | 10 | 11 | 12 | 13 |
| Cromolyn sodium (DSCG) (wt %) | 2.0 | 3.0 | 4.0 | 4.0 | 4.0 | 4.0 | 4.0 | 5.0 | 6.0 | 3.0 | 3.0 | 3.0 | 3.0 |
| NaCl (wt %) | 0.7 | 0.5 | 0.3 | 0.25 | 0.2 | 0.2 | 0.2 | 0.15 | 0.1 | 0.2 | 0.3 | 0.4 | 0.5 |
| Mannitol (wt %) | 0.4 | 0.8 | 1.0 | 1.1 | 1.2 | 1.25 | 1.25 | 1.4 | 1.5 | | | | |
| EDTA-Na (wt %) | 0.01 | 0.02 | 0.03 | 0.01 | 0.02 | 0.03 | 0.02 | 0.03 | 0.04 | 0.01 | 0.02 | 0.03 | 0.04 |
| Hyaluronic acid (wt %) | | | 0.25 | 0.5 | 1.0 | | | | | | 0.25 | 0.5 | 1.0 |
| Propylene glycol (wt %) | | | | | | | | | | 1.0 | 2.0 | 3.0 | 4.0 |
| Purified Water (wt %) | 96.9 | 95.7 | 94.4 | 94.1 | 93.6 | 94.5 | 94.5 | 93.4 | 92.4 | 95.8 | 94.4 | 93.1 | 91.5 |

3. 40 mg PA-101 (4% DSCG, 40 mg/1 mL), oral inhalation via eFlow 40 L.
4. 20 mg cromolyn sodium inhalation aerosol (1% DSCG, 20 mg/2 mL) (commercially available product), oral inhalation via LC Plus.
5. 200 mg oral sodium cromoglycate solution (commercially available product), oral administration.

All study subjects received each study treatment in the morning (at 8:00 am, +/−30 minutes) as a single dose treatment. Prior to each dosing day, subjects were admitted to the clinic in the morning for baseline (pre-dose) assessments. Subjects were required to remain in the clinic for 12 h after study drug administration on each dosing day. Treatment Visits were separated by a washout period of 2 to 5 days.

The main delivery device for administering PA-101 was the open system eFlow nebulizer using the 30 L aerosol head, which generates aerosol particles with a median size of about 3.0 μm. The 40 L aerosol head (generating aerosol particles with a median size of about 4.0 μm) was tested as a comparator arm.

Statistical Measurements

Pharmacokinetic parameters and plasma concentrations are listed and summarized. The summary statistics are presented as the geometric mean, arithmetic mean, arithmetic standard deviation (SD), min, median, max and n. The geometric statistics are not presented for $T_{max}$. Analysis of variance (ANOVA) including terms for subject and treatment are used to calculate point estimates, and confidence intervals (CI) for treatment differences with respect to PK parameters (90% CI) are calculated.

The incidence of AEs was compared between treatment groups. Summary tables and individual subject listings are provided for all safety measurements and the results are presented by treatment group. Descriptive statistics are used to summarise data where appropriate.

Results

The pharmacokinetic parameters measured in the single dose study are shown in the following table:

TABLE 2

| PK parameter | Oral solution, 200 mg | Inhalation aerosol, 20 mg | PA-101 (40 L), 40 mg | PA-101 (30 L), 40 mg | PA-101 (30 L), 80 mg | Ratio (PA-101 (30 L; 40 mg))/(oral solution (200 mg)) | Ratio (PA-101 (30 L; 40 mg)/ (inhalation aerosol (20 mg)) |
|---|---|---|---|---|---|---|---|
| $C_{max}$ (ng/mL) | 5.2 (±3.1) | 17.8 (±10.4) | 88.6 (±45.5) | 156 (±104) | 236 (±124) | x30 | x8.8 |
| $T_{max}$ (h) | 3.2 (±2.1) | 0.6 (±0.1) | 0.6 (±0.1) | 0.7 (±0.1) | 0.7 (±0.1) | | |
| $AUC_{0-t}$ (h * ng/mL) | 29.4 (±10.4) | 39.1 (±15.1) | 206 (±94.3) | 329 (±144) | 514 (±186) | x11 | x8.4 |
| $AUC_{(0-\infty)}$ (h * ng/mL) | 33.3 (±11.7) | 40.6 (±15.6) | 212 (±96.0) | 338 (±146) | 526 (±198) | | |
| $T_{1/2}$ (h) | 4.3 (±1.3) | 2.5 (±0.8) | 2.5 (±0.7) | 2.2 (±0.6) | 2.1 (±0.5) | | |
| Bio-availability (%) | 0.6 | 6.5 | 16.3 | 25.0 | 22.7 | X42 | X3.8 |

Values shown in parentheses are (±SD).

Duration of Study

The duration of the study was one day.

Criteria for Evaluation

Pharmacokinetic measurements: The PK parameters evaluated for plasma cromolyn sodium (DSCG) are maximum concentration ($C_{max}$), time to maximum concentration ($T_{max}$), terminal elimination half-life ($T_{1/2}$), area under the plasma concentration-time curve from time=0 to time of last measurable drug concentration $AUC_{(0-t)}$, and area under the plasma concentration-time curve from time=0 to infinity ($AUC_{0-\infty}$). Urine DSCG levels are measured for total DSCG excretion in the urine, and the bioavailability of the DSCG was calculated from the measured levels.

Safety measurements: Adverse events including gastrointestinal disturbance (e.g., abdominal pain, nausea, vomiting), changes in vital signs, 12-lead ECG and clinical laboratory tests (hematology, chemistry and urinalysis).

Modeling of lung deposition with an aerosol from the 30 L and 40 L devices using the Finaly model (Finlay, W H, and A R Martin, "Recent advances in predictive understanding respiratory tract deposition", Journal of Aerosol Medicine, Vol 21:189-205 (2008)) indicated that the lung deposition with the two devices should be very similar. However, the AUC value obtained with 40 mg dose using the 30 L device (338 ng*hr/mL) was surprisingly high compared to the value (212 ng*hr/mL) from the 40 L device. Cromolyn sodium is not metabolized in the body and is excreted intact via bile and urine. Cromolyn sodium deposited in the lung during inhalation will appear in the plasma and the AUC would therefore be a surrogate for cromolyn sodium deposited in the lung. Any cromolyn sodium swallowed during inhalation will contribute negligibly to the AUC since the oral bioavailability of cromolyn is only about 1% (Richards et al, J Pharmacol Exp Ther, Vol. 241, No. 3: 1028-1032 (1987)). The AUC data therefore indicate that at the same dose (40 mg), the lung deposition with the 30 L device was surprisingly higher than that with the 40 L device.

The numbers of adverse events observed in the single dose study are shown in the following table:

TABLE 3

| Adverse Event | Placebo | PA-101 (40 L), 40 mg | PA-101 (30 L), 40 mg | PA-101 (30 L), 80 mg | Inhalation aerosol, 20 mg | Oral solution, 200 mg |
|---|---|---|---|---|---|---|
| Cough | 1 | 1 | — | 1 | 1 | — |
| Oropharyngeal pain | — | — | — | — | 1 | 1 |
| Rhinorrhoea | 1 | — | — | — | — | — |
| Dizziness | — | — | 2 | — | — | — |
| Headache | — | — | — | 1 | — | 1 |
| Dysgeusia | — | — | — | — | — | 1 |
| Somnolence | — | — | — | 1 | — | — |
| Catheter-site Reaction | — | — | 1 | — | — | 1 |
| Nasopharygitis | — | — | — | — | 1 | — |
| Sinusitis | — | — | — | 1 | — | — |
| Abdominal Discomfort | — | — | — | — | — | 1 |
| Increased Appetite | — | 1 | — | — | — | — |

Example 4: Efficacy Study

Objective

The objectives of the study are: to determine the efficacy profile of cromolyn sodium inhalation formulation when administered using a high efficiency nebulizer in patients with chronic cough; and to assess the safety and tolerability of cromolyn sodium inhalation formulation when administered to patients with chronic cough using a high efficiency nebulizer.

Methodology

This is a Phase 2, randomized, double-blind, placebo-controlled, 2-period crossover, 2-cohort, multi-center efficacy study in 48 patients with chronic cough: 24 patients with idiopathic pulmonary fibrosis (IPF, Cohort 1) and 24 patients with chronic idiopathic cough (CIC, Cohort 2).

The study consists of two treatment periods of 14 days each separated by a Washout Period of 14 days (±2 days) between Period 1 and Period 2. A Screening Visit is conducted within 14 days before the Baseline Visit of Period 1. The two periods are identical except that in Period 2, patients crossover to the alternate treatment from that received in Period 1, according to a 1:1 randomization scheme. At the Screening Visit patients with a daytime cough severity score >40 mm using a linear 100 mm visual analogue scale are placed on 24-hour objective cough count monitoring using the LCM cough monitor. Patients with an average daytime cough count of at least 15 coughs per hour using LCM at the Screening Visit are eligible for randomization.

During each period, patients self-administer study drug (i.e., 40 mg PA101 or Placebo PA101 via eFlow) three times daily (i.e., 8:00 am±1 hour, 2:00 pm±1 hour, and 8:00 pm±1 hour) for 14 consecutive days of each period (e.g., Days 1-14). Patients attend a Pre-study Visit (Visit 1, Day −1) at the clinic in the morning prior to the Baseline/Treatment Visit (Visit 2, Day 1) and a cough count device (LCM) is dispensed for measurement of baseline 24-hour cough count. Patients return to the clinic next day in the morning (Visit 2, Day 1) to return the devices, assessment of quality of life measures, and to receive the first dose of the study treatment. Additional treatment visits during the Treatment Period occur on Day 7±1 day (Visit 3) and Day 15±1 day (Visit 5). Patients visit the clinic on Day 7±1 day (Visit 3) and Day 14±1 day (Visit 4) in the morning and the LCM device is dispensed for measurement of 24-hour cough count. Study assessments includes assessment of quality of life (LCQ and K-BILD), cough severity (VAS), pulmonary function tests (forced expiratory volume in one second [FEV1], forced vital capacity [FVC], and FEV1/FVC ratio), fraction of exhaled nitric oxide (FeNO), and safety assessments (AEs, vital signs, and ECG) on Days 1, 7 and 15 of each treatment period. Pulmonary function tests and K-BILD assessment are only performed in the IPF cohort. A safety follow-up call is placed within 7±2 days following the last study treatment.

Clinical safety laboratory samples are collected at the start and end of the treatment of each treatment period (Screening Visit and Visit 5 during the Treatment Period 1, and at Visit 2 and Visit 5 during the Treatment Period 2). All post-dose study procedures are conducted from time 0. Time 0 will be defined as the start of the first study drug administration (i.e., when the nebulizer has been turned on) of each period.

In the IPF cohort, patients are allowed to use antifibrotic therapy, i.e., pirfenidone, nintedanib, and N-acetylcysteine, during the course of the study provided that the dose is stabilized at least 3 months prior to the Screening Visit and throughout the study period.

Patients are not allowed to use prednisone, narcotic antitussives, baclofen, gabapentin, inhaled corticosteroids, benzonatate, dextromethorphan, carbetapentane, and H1 antihistamines, leukotriene modifiers, or cromolyn sodium for at least 2 weeks prior to the Screening Visit and throughout the study. Drugs containing bronchodilators (including beta-2 agonists and anticholinergics) are not allowed for at least 1 week prior to the Baseline Visit and during the study.

Duration of Study

The total duration of study is approximately 8 weeks, consisting of a Screening Period within 14 days before the first Treatment Visit (Visit 2, Day 1), two Treatment Periods of 14 days each (±1 day), a wash-out period of 14 days (±2 days) between the treatments, and a safety follow-up phone call within 7 days (±2 days) following the last study treatment.

Criteria for Evaluation

The primary criteria for efficacy evaluation are: change from baseline in daytime average cough count measured by LCM; change from baseline in 24-hour average cough count measured by LCM; change from baseline in the LCQ score;

change from baseline in quality of life as measured by K-BILD score (IPF cohort only); change from baseline in cough severity as measured by VAS score; change from baseline in pulmonary function tests (PFTs) (IPF cohort only); and change from baseline in FeNO as measured by Niox Vero.

The safety parameters include adverse events (AEs); change in vital signs (i.e., blood pressure and heart rate); change in 12-lead ECG; and clinical laboratory tests (i.e., hematology, biochemistry, urinalysis).

Results

At the end of the treatment period, patients exhibit a significant decrease from baseline in daytime average cough count measured by LCM, a significant decrease from baseline in 24-hour average cough count measured by LCM, a significant decrease from baseline in the LCQ score, a significant increase from baseline in quality of life as measured by K-BILD score, a significant decrease from baseline in cough severity as measured by VAS score, a significant increase from baseline in PFTs and a significant increase from baseline in FeNo as measured by Niox Vero. Minimal AEs are observed.

What is claimed is:

1. A pharmaceutically acceptable aerosol for the treatment of a lung condition in a subject, consisting of droplets of a solution consisting of (i) from about 4% to about 6% by weight of cromolyn sodium and (ii) an osmolarity adjusting agent consisting of (a) between 0.1% and 0.5% by weight of sodium chloride, inclusive of the endpoints, and (b) optionally salts of ethylenediaminetetraacetic acid (EDTA), and (iii) water; wherein the aerosol has a respirable fraction (≤3.3 µm) as measured by USP <1601> of between about 30% and about 95%, inclusive of the endpoints, and wherein the treatment of the lung condition in the subject is achieved via delivery of a therapeutically effective amount of cromolyn sodium to the lungs of the subject by the subject orally inhaling the pharmaceutically acceptable aerosol.

2. The pharmaceutically acceptable aerosol of claim 1, wherein the salts of EDTA comprise sodium EDTA.

3. The pharmaceutically acceptable aerosol of claim 1, wherein the solution contains from about 5 mg to about 80 mg of cromolyn sodium.

4. The pharmaceutically acceptable aerosol of claim 1, wherein the solution contains from about 36 mg to about 44 mg of cromolyn sodium.

5. The pharmaceutically acceptable aerosol of claim 1, wherein the aerosol has a respirable fraction (≤5 µm) as measured by USP <1601> of between about 75% and about 95%, inclusive of the endpoints.

6. The pharmaceutically acceptable aerosol of claim 1, wherein the sodium chloride is at a concentration of between 0.1% to 0.2% by weight, inclusive of the endpoints.

7. A pharmaceutically acceptable aerosol for delivery of a therapeutically effective amount of cromolyn sodium to the lungs of a subject, wherein the pharmaceutically acceptable aerosol is a nebulized solution consisting of (i) from about 4% to about 6% by weight of cromolyn sodium, (ii) between 0.1% and 0.5% by weight of sodium chloride, inclusive of the endpoints, (iii) a salt of EDTA, and (iv) water, wherein the delivery of a therapeutically effective amount of cromolyn sodium to the lungs of the subject is achieved by the subject orally inhaling the pharmaceutically acceptable aerosol.

8. The pharmaceutically acceptable aerosol of claim 7, wherein the salt of EDTA is sodium EDTA.

9. The pharmaceutically acceptable aerosol of claim 7, wherein the solution contains from about 5 mg to about 80 mg of cromolyn sodium.

10. The pharmaceutically acceptable aerosol of claim 7, wherein the solution contains from about 36 mg to about 44 mg of cromolyn sodium.

11. The pharmaceutically acceptable aerosol of claim 7, wherein the aerosol has a respirable fraction (≤3.3 µm) as measured by USP <1601> of between about 30% and about 95%, inclusive of the endpoints.

12. The pharmaceutically acceptable aerosol of claim 7, wherein the aerosol has a respirable fraction (≤3.3 µm) as measured by USP <1601> of between about 30% and about 95%, inclusive of the endpoints, and a respirable fraction (≤5 µm) as measured by USP <1601> of between about 75% and about 95%, inclusive of the endpoints.

13. The pharmaceutically acceptable aerosol of claim 7, wherein the sodium chloride is at a concentration of between 0.1% to 0.2% by weight, inclusive of the endpoints.

14. A method of treating a lung condition in a subject, comprising administering a pharmaceutically acceptable aerosol to the subject by oral inhalation, the pharmaceutically acceptable aerosol consisting of droplets of a solution consisting of (i) from about 4% to about 6% by weight of cromolyn sodium, (ii) between 0.1% and 0.5% by weight of sodium chloride, inclusive of the endpoints, (iii) optionally salts of ethylenediaminetetraacetic acid (EDTA), and (iv) water; wherein the aerosol has a respirable fraction (≤3.3 µm) as measured by USP <1601> of between about 30% and about 95%, inclusive of the endpoints.

15. The method of claim 14, wherein the salts of EDTA comprise sodium EDTA.

16. The method of claim 14, wherein the solution contains from about 5 mg to about 80 mg of cromolyn sodium.

17. The method of claim 14, wherein the solution contains about from about 36 mg to about 44 mg of cromolyn sodium.

18. The method of claim 14, wherein the aerosol has a respirable fraction (≤3.3 µm) as measured by USP <1601> of between about 30% and about 95%, inclusive of the endpoints.

19. The method of claim 14, wherein the aerosol has a respirable fraction (≤5 µm) as measured by USP <1601> of between about 75% and about 95%, inclusive of the endpoints.

20. The method of claim 16, wherein the aerosol has a further respirable fraction (≤5 µm) as measured by USP <1601> of between about 75% and about 95%, inclusive of the endpoints.

21. The method of claim 14, wherein the sodium chloride is at a concentration of between 0.1% to 0.2% by weight, inclusive of the endpoints.

* * * * *